US007666610B2

(12) United States Patent
Saitoh et al.

(10) Patent No.: US 7,666,610 B2
(45) Date of Patent: Feb. 23, 2010

(54) EXPRESSING TRANSPORTERS ON VIRAL ENVELOPES

(75) Inventors: Ryoichi Saitoh, Shizuoka (JP); Toshihiko Ohtomo, Shizuoka (JP); Masayuki Tsuchiya, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 283 days.

(21) Appl. No.: 10/509,343

(22) PCT Filed: Mar. 28, 2003

(86) PCT No.: PCT/JP03/03975

§ 371 (c)(1), (2), (4) Date: Jun. 21, 2005

(87) PCT Pub. No.: WO03/083116

PCT Pub. Date: Oct. 9, 2003

(65) Prior Publication Data

US 2006/0084119 A1 Apr. 20, 2006

(30) Foreign Application Priority Data

Mar. 29, 2002 (JP) ............................ 2002-096038

(51) Int. Cl.
*G01N 33/567* (2006.01)
*C07H 21/04* (2006.01)
*C12P 21/06* (2006.01)
*C12N 5/06* (2006.01)
*C07K 14/705* (2006.01)

(52) U.S. Cl. ....................... 435/7.2; 435/69.1; 435/348; 435/456; 530/350; 536/23.5

(58) Field of Classification Search ....................... None
See application file for complete search history.

(56) References Cited

U.S. PATENT DOCUMENTS

| | | | | |
|---|---|---|---|---|
| 5,500,346 | A | 3/1996 | Bright et al. | |
| 5,849,525 | A | 12/1998 | Hediger | |
| 6,270,978 | B1 | 8/2001 | Bright et al. | 435/7.1 |
| 6,713,278 | B1 | 3/2004 | Bouvier et al. | |
| 2005/0004227 | A1 | 1/2005 | Saitoh | |
| 2005/0222391 | A1 | 10/2005 | Kodama et al. | |
| 2005/0281825 | A1 | 12/2005 | Kodama et al. | |
| 2006/0084119 | A1 | 4/2006 | Saitoh et al. | |
| 2006/0210569 | A1 | 9/2006 | Kodama et al. | |
| 2008/0040820 | A1 | 2/2008 | Kodama et al. | |

FOREIGN PATENT DOCUMENTS

| | | |
|---|---|---|
| AU | 9676557 | 6/1997 |
| EP | 1142473 | 10/2001 |
| EP | 1 731 032 | 12/2006 |
| JP | 6-261761 | 9/1994 |
| JP | 8-134100 | 5/1996 |
| JP | 11-172 | 1/1999 |
| JP | 2001-197846 | 7/2001 |
| JP | 2001-139496 | 5/2005 |
| KR | 99071666 | 9/1999 |
| WO | WO 97/19919 | 6/1997 |
| WO | WO 98/46777 | 10/1998 |
| WO | WO 00/28016 | 5/2000 |
| WO | WO 03/033024 | 4/2003 |
| WO | WO 03/047621 | 6/2003 |
| WO | WO 03/083116 A1 | 10/2003 |
| WO | WO 03/104453 | 12/2003 |

OTHER PUBLICATIONS

Hsu et al., Overexpression of human intestinal oligopeptide transporter in mammalian cells via adenoviral transduction, 1998, Pharmaceutical Research, vol. 15, No. 9, pp. 1376-1381.*

Garcia et al., cDNA cloning of MCT2, a second monocarboxylate transporter expressed in different cells than MCT1, 1995, Journal of Biological Chemistry, vol. 270, No. 4, pp. 1843-1849.*

Miyasaka, et al., Characterization of human taurine transporter expressed in insect cells using recombinant baculovirus, 2001, Protein Expression and Purification, vol. 23, pp. 389-397.*

Hsu et al., Overexpression of human intestinal oligopeptide transporter in mammalian cells via adenoviral transduction, 1998, Pharmaceutical Research, vol. 15, No. 9, pp. 1376-1381.*

ATCC Web Catalog, "Tumor Cell Lines" www.atcc.org (2007), 15 pages.

Boublik et al., "Eukaryotic Virus Display: Engineering the major Surface Glycoprotein of the *Autographa californica* Nuclear Polyhedrosis Virus (ScNPV) for the Presentation of Foreign Proteins on the Virus Surface," *Biotechnology*, 13 1079-1084 (1995).

"Cancer Classification," SEER Training Website, www.training.seer.cancer.gov/module_cancer_disease/unti3-categories2_by_histology (2005), 3 pages.

Grever et al., "The National Cancer Institute: Cancer Drug Discovery and Development Program," Seminars in Oncology, 19(6): 622-638 (1992).

Hefferon et al., "Host Cell receptor Binding by Baculovirus GP64 and Kinetics of Virion Entry," *Virology*, 258: 455-468 (1999).

Kamada et al., "Production of GP64, the Major Envelope Glycoprotein of Budded Baculovirus, Transgenic Mice and Induction of immunological Tolerance of GP64 Transgenic Mice," *Nihon Bunshi Seibutsu Gakkai Nenkai Program Koen Yoshishu*, 26: 659 (2003) (Translation Provided).

Lu et al., "Characterization of a Truncated Soluble Form of the Baculovirus (AcMNPV) Major Envelope Protein Gp64," *Protein Expression and Purification*, 24: 196-201 (2002).

(Continued)

*Primary Examiner*—Robert Landsman
*Assistant Examiner*—Ian Dang
(74) *Attorney, Agent, or Firm*—Fish & Richardson P.C.

(57) ABSTRACT

Methods for measuring transporter activity using budding baculoviruses that do not express endogenous transporters on their envelope have a low background level and can measure the target activity with a high sensitivity. Such methods can be used to measure functional changes due to transporter SNPs over a more extensive range of substrates, and can be applied to tailor-made therapies.

22 Claims, 4 Drawing Sheets

OTHER PUBLICATIONS

Monsma et al., "Identification of a Membrane Fusion Domain and an Oligomerization Domain in the Baculovirus GP64 Envelope Fusion Protein," *Journal of Virology*, 69: 2583-2595 (1995).
Monsma et al., "The GP64 Envelope Fusion Protein is an Essential Baculovirus Protein Required for Cell-to-Cell Transmission of Infection," *Journal of Virology*, 70: 4607-4616 (1996).
Ohtomo et al., "Generation of Anti-Human CCR Antagonistic Antibodies in GP64 Expressing and CCR2-Deficient Mice Using CCR2 Expressed Budded Baculovirus as an Antigen," *Nihon Bunshi Seibutsu Gakkai Nenkai Program Koen Yoshishu*, 26: 660 (2003) (Translation Provided).
Seliger et al., "Analysis of the MHC Class I Antigen Presentation Machinery in Human Embryonal Carcinomas: Evidence for Deficiencies in TAP, LMP, and MHC Class I Expression and Their Upregulation by IFN-γ," Scandinavian Journal of Immunology, 46: 625-632 (1997) (Abstract).
Suzuki et al., "Effects of Retinoic Acid on Lung Smooth Muscle Cells," Meeting on Experimental Biology: Translating The Genome (Apr. 17-21, 2004) as published in FASEB Journal, 18(4-5): 355-356 (2004) (Abstract).
Tamura et al.,"CD14 Transgenic Mice Expressing Membrane and Soluble Forms: Comparisons of Levels of Sytokines and Lethalities in Response to Lipopolysaccharide Between Transgenic and Non-Transgenic Mice," *International Immunology*, 11:333-339 (1999).
Watanabe et al., "Enhances Immune Responses in Transgenic Mice Expressing a Truncated Form of the Lymphocyte Semaphorin CD100[1]," *J. Immunol*. 167: 4321-4328 (2001).
Braunagel et al., "Autographe californica Nuclear Polyhedrosis Virus, PDV, and ECV Viral Envelopes and Nucleocapsids: Structural Proteins, Antigens, Lipid and Fatty Acid Profiles", Virology, vol. 202, pp. 315-320 (1994).
Grabherr et al., "Developments in the use of baculoviruses for the surface display of complex eukaryotic proteins", Trends in Biology, vol. 19(6), pp. 231-235 (2001).
Marheineke et al., "Lipid composition of *Spodoptera frugiperda* (Sf9) and *Trichoplusia ni* (Tn) insect cells used for baculovirus infection", FEBS vol. 441, pp. 49-52 (1998).
Zhou X. et al., "Characterization of an oligopeptide transporter in renal lysosomes", Biochim Biophys Acta, vol. 1466(1-2), pp. 372-378 (2000).
Lee VHL et al., "Biopharmaceutics of transmucosal peptide and protein drug administration: role of transport mechanisms with a focus on the involvement of PepT1", J. Control Release, vol. 62(1-2), pp. 129-140 (1999).
Loisel TP et al., "Recovery of homogeneous and functional $\beta_2$-adrenergic receptors from extracellular baculovirus particles", Nat Biotechnol, vol. 15(12), pp. 1300-1304 (1997).
Mangor JT et al., "A GP64-Null Baculovirus Pseudotyped with Vesicular Stomatitis Virus G Protein", Journal of Virology, vol. 75(6), pp. 2544-2556 (2001).
Szakács G et al., "Characterization of the ATPase Cycle of Human ABCA1: Implications for Its Function as a Regulator Rather Than an Active Transporter", Biochem Biophys Res Commun, vol. 288(5), pp. 1258-1264 (2001).
Noe J et al., "Characterization of the Mouse Bile Salt Export Pump Overexpressed in the Baculovirus System", Hepatology, vol. 33(5), pp. 1223-1231 (2001).
Sakaguchi T. et al., "The Ion Channel Activity of the Influenza Virus M2 Protein Affects Transport through the Golgi Apparatus", J Cell Biol., vol. 133(4), pp. 733-747 (1996).
Mikhailov MV et al., "Expression of functionally active ATP-sensitive K-channels in insect cells using baculovirus", FEBS Lett, vol. 429(3), pp. 390-394 (1998).
Strehlow D. et al., "Retroviral membrane display of apoptotic effector molecules", Proc Natl Acad Sci USA, vol. 97(8), pp. 4209-4214 (2000).
Sun D. et al., "Drug Inhibition of Gly-Sar Uptake and hPepT1 Localization using hPepT1-GFP Fusion Protein", AAPS PharmSci., vol. 3(1), pp. 1-9 (2001).
Sai Y. et al., "Immunolocalization and pharmacological relevance of oligopeptide transporter PepT1 in intestinal absorption of β-lactam antibiotics", FEBS Lett, vol. 392(1), pp. 25-29 (1996).
Basu SK et al., "Development and Utility of Anti-PepT1 Anti-Peptide Polyclonal Antibodies", Pharmaceutical Research, vol. 15(2), pp. 338-342 (1998).
Gonzalez DE et al., "An Olgiopeptide Transporter Is Expressed at High Levels in the Pancreatic Carcinona Cell Lines AsPc-1 and Capan-2[b]", Cancer Res., vol. 58(3), pp. 519-525 (1998).
Knutter et al., "A Novel Inhibitor of the Mammalian Peptide Transporter PEPT1", Biochemistry, vol. 40(14), pp. 4454-4488 (2001).
Mrsny RJ., "Olgiopeptide Transporters as Putative Therapeutic Targets for Cancer Cells", Pharm Res. vol. 15(6), pp. 816-818 (1998).
Nakanishi T. et al., "Cancer Cell-Targeted Drug Delivery Utilizing Oligopeptide Transport Activity", Int. J. Cancer, vol. 88(2), pp. 274-280 (2000).
Sugano K. et al., Quantitive Structure-Intestinal Permeability Relationship of Benzamidine Analogue Thrombin Inhibitor, Bioorg Med. Chem. Lett, vol. 10(17), pp. 1939-1942 (2000).
Terada T. et al., Tanpalcushitsu Kakusan Koso (Protein, nucleic acid and enzyme), vol. 46(5), pp. 621-628 (2001) (Concise explanation in English enclosed).
Basu et al., "Screening of Anti-PepT1 Antibodies Using Indirect ELISA," *Pharmaceutical Research*, 13(9 Suppl.):S-37, Abstract No. APQ 1137 (1996).
Blissard et al., "Location, Sequence, Transcriptional Mapping, and Temporal Expression of the gp64 Envelope Glycoprotein Gene of the *Orgyia pseudotsugata* Multicapsid Nuclear Polyhedrosis Virus," *Virology*, 170:537-555 (1989).
Friedman et al., "Characterization of the Intestinal Transport Parameters for Small Peptide Drugs," *J. Control. Release*, 13:141-146 (1990).
Friedman et al., "Passive and Carrier-Mediated Intestinal Absorption Components of Two Angiotensin Converting Enzyme (ACE) Inhibitor Prodrugs in Rats: Enalapril and Fosinopril," *Pharm. Res*., 6:1043-1047 (1989).
Ganapathy et al., "Proton-coupled solute transport in the animal cell plasma membrane," *Curr. Opin. Cell Biol*., 3:695-701 (1991).
Higgins, "ABC Transporters: From Microorganisms to Man," *Annu. Rev. Cell Biol*., 8:67-113 (1992).
Houdebine, "Transgenic animal bioreactors," *Transgenic Res*., 9:305-320 (2000).
Kolb et al., "Insertion of a foreign gene into the β-casein locus by Cre-mediated site specific recombination," *Gene*, 227:21-31 (1999).
Lariviere et al., "Transgenic Studies of Pain and Analgesia: Mutation or Background Genotype?" *J. Pharmacol. Exp. Ther*., 297:467-473 (2001).
Leiter, "Mice with targeted gene disruptions or gene insertions for diabetes research: problems, pitfalls, and potential solutions," *Diabetologia*, 45:296-308 (2002).
Liang et al., "Human Intestinal $H^+$/Peptide Cotransporter. Cloning, Functional Expression, and Chromosomal Localization," *J. Biol. Chem*., 270:6456-6463 (1995).
Lindley et al., "Production of monoclonal antibodies using recombinant baculovirus displaying gp64-fusion proteins," *J. Immunol. Methods*, 234:123-135 (2000).
Liu et al., "Molecular cloning of PEPT2, a new member of the $H^+$/peptide cotransporter family, from human kidney," *Biochim. Biophys. Acta*, 1235:461-466 (1995).
Mancini et al., "Induction of Anti-Hepatitis B Surface Antigen (HBsAg) Antibodies in HBsAg Producing Transgenic Mice: A Possible Way of Circumventing 'Nonresponse' to HBsAg," *J. Med. Virol*., 39:67-74 (1993).
Muranushi et al., "Transport Characteristics of Ceftibuten, a New Oral Cephem, in Rat Intestinal Brush-Border Membrane Vesicles: Relationship to Oligopeptide and Amino β-Lactam Transport," *Pharm. Res*., 6:308-312 (1989).
Murray, "Genetic Modification of Animals in the Next Century," *Theriogenology*, 51:149-159 (1999).
Nakashima et al., "Kinetics and Mechanism of In Vitro Uptake of Amino-β-Lactam Antibiotics by Rat Small Intestine and Relation to the Intact-Peptide Transport System," *Biochem. Pharmacol*., 33:3345-3352 (1984).

Ogihara et al., "Immuno-Localization of $H^+$/Peptide Cotransporter in Rat Digestive Tract," *Biochem. Biophys. Res. Commun.*, 220:848-852 (1996).
Okano et al., "$H^+$ Coupled Uphill Transport of Aminocephalosporins via the Dipeptide Transport System in Rabbit Intestinal Brush-border Membranes," *J. Biol. Chem.*, 261:14130-14134 (1986).
Sai et al., "Selective Delivery of Peptide Anticancer Drugs via Oligopeptide Transporter Expressed in Cancer Cells," *Proceedings of the Millennium World Congress of Pharmaceutical Science*, p. 61, Abstract No. 2-2124 (Apr. 16-20, 2000).
Saito et al., "Cloning and Chracterization of a Rat $H^+$/Peptide Cotransporter Mediating Absorption of β-Lactam Antibiotics in the Intestine and Kidney," *J. Pharmacol. Exp. Ther.*, 275:1631-1637 (1995).
Saito et al., "Molecular cloning and tissue distribution of rat peptide transporter PEPT2," *Biochim. Biophys. Acta*, 1280:173-177 (1996).
Satoi et al., "Genetic Immunization of Wild-Type and Hepatitis C Virus Transgenic Mice Reveals a Hierarchy of Cellular Immune Response and Tolerance Induction against Hepatitis C Virus Structural Proteins," *J. Virol.*, 75:12121-12127 (2001).
Shen et al., "Localization of PEPT1 and PEPT2 proton-coupled oligopeptide transporter mRNA and protein in rat kidney," *Am. J. Physiol.*, 276:F658-F665 (1999).
Sigmund, "Viewpoint: Are Studies in Genetically Altered Mice Out of Control,"*Arterioscler. Thromb. Vasc. Biol.*, 20:1425-1429 (2000).
Steiner et al., "The PTR family: a new group of peptide transporters," *Mol. Microbiol.*, 16:825-834 (1995).
Takahashi et al., "Interaction of β-Lactam Antibiotics with $H^+$ Peptide Cotransporters in Rat Renal Brush-Border Membranes," *J. Pharmacol. Exp. Ther.*, 286:1037-1042 (1998).
Terada et al., "Characterization of Stably Transfected Kidney Epithelial Cell Line Expressing Rat $H^+$/Peptide Cotransporter PEPT1: Localization of PEPT1 and Transport of β-Lactam Antibiotics," *J. Pharmacol. Exp. Ther.*, 281:1415-1421 (1997).
Tsuchiya, "Therapeutic Antibody," Presentation, Chugai Pharmaceutical Co., Ltd., 21 pages (Jan. 21, 2003).
Blissard et al., "Baculovirus gp64 Gene Expression: Analysis of Sequences Modulating Early Transcription and Transactivation by IE1," *J. Virol.*, 65:5820-5827 (1991).
Karaki et al., "Production of anti-HLA class II alloantibodies using HLA-B51 transgenic mice," *Nihonmenekigakkaisoukai Gakujutsushuukaikiroku*, Abstract No. C61, p. 197 (1990) (English translation included).
Nishimura et al., "Expression of the Human MHC, HLA-DQw6 Genes Alters the Immune Response in C57BL/6 Mice," *J. Immunol.*, 145:353-360 (1990).
Okamoto et al., "Generation of monoclonal antibodies directed against allotypic epitopes of HLA class II antigen by utilizing HLA-DQw6 transgenic mice," *Nihonmenekigakkaisoukai Gakujutsushuukaikiroku*, Abstract No. C62, p. 197 (1990) (English translation included).
D'Onofrie, "Making the case for acncer prevention in the schools", Journal of School Health 59(5):225-227, 1989.
Inoue et al., "Regulation of human peptide transporter 1 (PEPT1) in gastric cancer cells by anticancer drugs", Cancer Letters 230:72-80, 2005.
Pardee, "Tumor progression—targets for differential therapy", Journal of Cellular Physiology 209(3):589-591, 2006 (abstract only).
Breyer et al., "Mutational analysis of ligand binding activity of $\beta_2$ adrenergic receptor expressed in *Escherichia coli," Embo J.*, 9(9):2679-2684 (1990).
Campbell, "Monoclonal antibody technology," Elsevier Science Publishing Company, Inc., New York, pp. 1-33 (1984).
Clark, M., "Antibody humanization: a case of the 'Emperor's new clothes'?," *Immunol. Today*, 21(8):397-402 (2000).
Covitz et al., "Membrane Topology of the Human Dipeptide Transporter, hPEPT1, Determined by Epitope Insertions," *Biochemistry*, 37:15214-15221 (1998).
Kanamitsu, Kotai Kogaku Nyumon, 33-6 (1994) (English translation included).
Kawaguchi et al., "Gan Chiryo to Syukusyu: Frontiers in Cancer Treatment," 13(1):12-20 (2001).
Mclaughlin, "Rituximab: perspective on single agent experience, and future directions in combination trials," *Critical Reviews in Oncology/Hematology*, 40:3-16 (2001).
Saitoh et al., "Recovery of functional peptide transporter PepT1 in budded baculovirus fraction," *Protein Expr. Purif.* , 46(1):130-135 (2006).
Tada et al., "Complement-dependent cytolysis," *Dictionary of Immunology 3rd Edition*, 144 (1993).
Tate et al., "Molecular Chaperones Stimulate the Functional Expression of the Cocaine-Sensitive Serotonin Transporter," *J. Biol. Chem.*, 274(25):17551-17558 (1999).
Tsuro et al., "Inhibition of Multidrug-resistant Human Tumor Growth in Athymic Mice by Anti-P-glycoprotein Monoclonal Antibodies," *Jpn. J. Cancer Res.*, 80:627-631(1989).
Walker et al., "Substrate upregulation of the human small intestinal peptide transporter, hPepT1," *Journal of Physiology*, 507.3:697-706 (1998).
Winter et al., "Man-made antibodies," *Nature*, 349:293-299 (1991).
U.S. Examiner Celia C. Chang, USPTO Restriction Requirement in U.S. Appl. No. 10/492,376, dated Jun. 6, 2007, 16 pages.
Fish & Richardson P.C., Response to Restriction Requirement dated Jun. 6, 2007 in U.S. Appl. No. 10/492,376, filed Jul. 6, 2007, 1 page.
U.S. Examiner Celia C. Chang, USPTO Office Action in U.S. Appl. No. 10/492,376, dated Sep. 17, 2007, 6 pages.
Fish & Richardson P.C., Amendment in Reply to Action dated Sep. 17, 2007 in U.S. Appl. No. 10/492,376, filed Jan. 17, 2008, 10 pages.
U.S. Examiner Celia C. Chang, USPTO Office Action in U.S. Appl. No. 10/492,376, dated Apr. 1, 2008, 10 pages.
Japanese Patent Office, International Preliminary Report on Patentability for App. Ser. No. PCT/JP02/10743, dated Apr. 21, 2003, 4 pages.
Japanese Patent Office, International Search Report for App. Ser. No. PCT/JP02/10743, mailed Feb. 4, 2003, 2 pages.
U.S. Examiner Christopher H. Yaen, USPTO Restriction Requirement in U.S. Appl. No. 10/497,900, dated Jun. 13, 2008, 6 pages.
Fish & Richardson P.C., Response to Restriction Requirement dated Jun. 13, 2008 in U.S. Appl. No. 10/497,900, filed Jul. 11, 2008, 1 page.
U.S. Examiner Christopher H. Yaen, USPTO Office Action in U.S. Appl. No. 10/497,900, dated Sep. 19, 2007, 20 pages.
Fish & Richardson P.C., Amendment in Reply to Action dated Sep. 19, 2007 in U.S. Appl. No. 10/497,900, filed Feb. 19, 2008, 9 pages.
U.S. Examiner Christopher H. Yaen, USPTO Office Action in U.S. Appl. No. 10/497,900, dated Oct. 30, 2008, 16 pages.
Fish & Richardson P.C., Amendment in Reply to Action dated Oct. 30, 2008 in U.S. Appl. No. 10/497,900, filed Mar. 27, 2009, 8 pages.
Japanese Patent Office, International Preliminary Report on Patentability for App. Ser. No. PCT JP02/12708, dated Aug. 12, 2003, 6 pages.
Japanese Patent Office, International Search Report for App. Ser. No. PCT/JP02/12708, mailed Mar. 11, 2003, 4 pages.
Japanese Patent Office, International Preliminary Report on Patentability for App. Ser. No. PCT/JP03/03975, dated Sep. 8, 2003, 6 pages.
Japanese Patent Office, International Search Report for App. Ser. No. PCT/JP03/03975, mailed May 6, 2003, 2 pages.
U.S. Examiner Louis D. Lieto, USPTO Restriction Requirement in U.S. Appl. No. 10/516,603, dated Dec. 28, 2005, 5 pages.
Fish & Richardson P.C. Response to Restriction Requirement dated Dec. 28, 2005 in U.S. Appl. No. 10/516,603, filed Mar. 28, 2006, 1 page.
U.S. Examiner Louis D. Lieto, USPTO Office Action in U.S. Appl. No. 10/516,603, dated Apr. 24, 2006, 15 pages.
Fish & Richardson P.C., Amendment in Reply to Action dated Apr. 24, 2006 in U.S. Appl. No. 10/516,603, filed Oct. 24, 2006, 9 pages.
Fish & Richardson P.C., Supplemental Response to Amendment filed Oct. 24, 2006 in U.S. Appl. No. 10/516,603, filed Nov. 7, 2006, 5 pages.
U.S. Examiner Marcia Stephens Noble, USPTO Office Action in U.S. Appl. No. 10/516,603, dated Mar. 9, 2007, 18 pages.
Fish & Richardson P.C., Amendment in Reply to Action dated Mar. 9, 2007 in U.S. Appl. No. 10/516,603, filed Jun. 11, 2007, 10 pages.

Fish & Richardson P.C., Amendment in U.S. Appl. No. 10/516,603, filed Sep. 10, 2007, 6 pages.
U.S. Examiner Marcia Stephens Noble, USPTO Notice of Allowance in U.S. Appl. No. 10/516,603, dated Apr. 25, 2008, 11 pages.
Fish & Richardson P.C., Amendment in U.S. Appl. No. 10/516,603, filed Jul. 24, 2008, 5 pages.
U.S. Examiner Marcia Stephens Noble, USPTO Office Action in U.S. Appl. No. 10/516,603, dated Jan. 27, 2009, 7 pages.
Fish & Richardson P.C., Amendment in Reply to Action dated Jan. 27, 2009 in U.S. Appl. No. 10/516,603, filed May 15, 2009, 4 pages.
Japanese Patent Office, International Preliminary Report on Patentability for App. Ser. No. PCT/JP03/07071, dated Nov. 21, 2003, 7 pages.
Japanese Patent Office, International Search Report for App. Ser. No. PCT/JP03/07071, mailed Jul. 22, 2003, 3 pages.
U.S. Examiner Christopher H. Yaen, USPTO Office Action in U.S. Appl. No. 10/550,987, dated Oct. 5, 2007, 16 pages.
Fish & Richardson P.C., Amendment in Reply to Action dated Oct. 5, 2007 in U.S. Appl. No. 10/550,987, filed Mar. 5, 2008, 9 pages.
U.S. Examiner Christopher H. Yaen, USPTO Office Action in U.S. Appl. No. 10/550,987, dated Jun. 13, 2008, 13 pages.
Fish & Richardson P.C., Amendment in Reply to Action dated Jun. 13, 2008 in U.S. Appl. No. 10/550,987, filed Feb. 19, 2009, 12 pages.
U.S. Examiner Christopher H. Yaen, USPTO Office Action in U.S. Appl. No. 10/550,987, dated Mar. 31, 2009, 12 pages.
European Examiner R. Rankin, European Search Report for App. Ser. No. EP 04723785.4, dated Jul. 12, 2006, 2 pages.
Japanese Patent Office, International Preliminary Report on Patentability for App. Ser. No. PCT/JP04/004331, dated Dec. 17, 2004, 5 pages.
Japanese Patent Office, International Search Report for App. Ser. No. PCT/JP04/004331, mailed Jun. 22, 2004, 2 pages.
U.S. Examiner Michael C. 'Wilson, USPTO Office Action in U.S. Appl. No. 10/594,690, mailed Oct. 16, 2008, 18 pages.
Fish & Richardson P.C., Amendment in Reply to Action dated Oct. 16, 2008 in U.S. Appl. No. 10/594,690, filed Apr. 16, 2009, 9 pages.
U.S. Examiner Michael C. Wilson, USPTO Final Office Action in U.S. Appl. No. 10/594,690, mailed Jun. 8, 2009, 11 pages.
Japanese Patent Office, International Preliminary Report on Patentability for App. Ser. No. PCT/JP2005/006298, dated Feb. 8, 2006, 10 pages.
Japanese Patent Office, International Search Report for App. Ser. No. PCT/JP2005/006298, mailed Jul. 12, 2005, 3 pages.
EPO Examiner John Renggli, European Search Report for App. Ser. No. EP 03 73 3287, dated Jun. 22, 2009 (2 pages).
Bachmann et al., "Correlation of Tolerogenicity of a Viral Antigen with Its Immunogenicity," *The Journal of Immunology*, 158:5106-5111 (1997).
Ramamoorthy et al., "Proton/peptide cotransporter (PEPT 2) from human kidney: Functional characterization and chromosomal localization," *Biochimica et Biophysica Acta*, 1240:1-4 (1995).
Steinhoff et al., "Variable Immune Response Against a Developmentally Regulated Self-Antigen," Journal of Autoimmunity, 12:27-34 (1999).
U.S. Examiner Christopher H. Yaen, USPTO Notice of Allowance in U.S. Appl. No. 10/497,900, dated Sep. 8, 2009, 7 pages.
U.S. Examiner Marcia Stephens Noble, USPTO Office Action in U.S. Appl. No. 10/516,603, dated Aug. 19, 2009, 10 pages.
Examiner F. Chambonnet, European Search Report for App. Ser. No. EP 05 72 7975, dated Sep. 11, 2009, 2 pages.

* cited by examiner

EXPRESSING TRANSPORTERS ON VIRAL ENVELOPES

TECHNICAL FIELD

The present invention relates to methods for expressing transporters having transporter activity, where the methods comprise using transporter-encoding genes to express transporters on the envelope of budding viruses. In addition, the present invention relates to viruses that express transporters having transporter activity, methods that use these viruses for measuring the transporter activity, and methods of screening for substances that inhibit or promote the transporter activity of the transporters.

BACKGROUND ART

Mammals must take in nutrients from outside the body, and many transporter proteins (transporters) are known to exist in mammalian cells. These transporters mainly act to transport substances essential to the maintenance of life (amino acids, sugars, and such) into cells. In the physiological environment, cells often have multiple transporters that transport the same substrate. In these cases, the individual contribution of transporters to cellular uptake can be estimated using kinetic analysis (calculation of Km, Vmax, and so on; e.g., Wright E. M., Am. J. Physiol. Renal Physiol., 2001, 280: F10-18). Thus, identification of transport substrates and kinetic analysis of transporters are extremely important for revealing their physiological function and their potential in drug delivery.

Currently, methods for analysing transporter function use the following resources as materials: (1) primary cultured cells and cell membrane vesicles (such as lung cells and brush border membrane vesicles) comprising transporters isolated from living bodies; (2) cell lines derived from transporter-comprising cancer cells and so on (such as Caco-2 cells); (3) mammalian cells introduced with transporter genes (such as LLC-PK1 cells and MDCK cells) and *Xenopus oocytes*; and (4) insect cell membranes (such as Sf9 cell membranes) in which transporters have been expressed using baculovirus expression systems. Of these, mostly used are gene expression systems from mammalian cells and *Xenopus oocyte* cells. However, even in mammalian and *Xenopus oocyte* cells introduced with transporter genes, activities from endogenous transporters can be detected, thus elevating background levels (Kanai Y. et al., J. Clin. Invest. 93: 397-404 (1994); Kekuda R. et al., J. Biol. Chem. 271: 18657-18661 (1996); Kekuda R. et al., Am. J. Physiol. 272: G1463-1472 (1997); Yabuuchi H. et al., J. Pharmacol. Exp. Ther. 286: 1391-1396 (1998); Hatanaka T. et al., J. Clin. Invest. 107: 1035-1043 (2001)). For this reason, in some types of transporters, there are reports that describe an activity ratio of only two between cells introduced with genes and those not introduced with genes (parent cell lines). Carrying out kinetic analysis can be problematic in such gene-introduced cells with a low activity ratio.

In *Xenopus oocyte* cells introduced with transporter genes, transporter activity can be measured using electrophysiological methods. In transporters driven by Na and H ions, and substrates having an electric charge at physiological pH, transporter activity can be detected by measuring the electrical current caused by substrate transport. However, measuring transport activity is difficult when there is no driving force and also when substrates are electrically neutral at physiological pH. Kinetic analysis is also difficult in cases where transporter activity is observed but only a weak current can be detected. In addition, since electrophysiological methods require specific equipment, they are not simple or convenient.

The activity and substrate specificity of transporters that transfer drugs into cells has been reported to influence the drug's bioavailability (for example, Ganaphthy, Leibach, Curr. Biol 3: 695-701 (1991); Nakashima et al., Biochem. Pharm. 33: 3345-3352 (1984); Friedman, Amidon, Pharm. Res. 6:1043-1047 (1989); Okano et al., J. Biol. Chem. 261: 14130-14134 (1986); Muranushi et al., Pharm. Res. 6: 308-312 (1989); Friedman, Amidon, J. Control. Res. 13: 141-146 (1990)). In recent years, research on factors that fluctuate in vivo pharmacokinetics has clarified that drug-metabolising enzymes as well as drug-transporters influence the function of drugs in the body. Known drug-transporters include p-glycoprotein (Annu. Rev. Biochem. 58: 137 (1989)), multidrug resistance protein (Science 258: 1650 (1992); Cancer Res. 55: 102 (1995)), lung resistance protein (Ann. Oncl. 7: 625 (1996); Int. J. Cancer 73: 1021 (1997)), and organic cation transporter (Proc. Natl. Acad. Sci. USA 91: 133 (1994); Molec. Pharmacol. 51: 913 (1997)). Analysis of SNPs is being carried out for these drug-transporters in the same way as for drug-metabolizing enzymes. Transporter SNPs that bring about functional changes have been recently found. These SNPs are receiving attention as one of the factors causing fluctuations between individuals (Ryu S. et al., J. Biol. Chem. 275: 39617-39624 (2000); Tirona R. G. et al., J. Biol. Chem. 276: 35669-35675 (2001)). Currently, functional analysis of transporter SNPs mainly uses mammalian cells introduced with genes. However, this is speculated to be problematic for accurately detecting functional changes caused by SNPs in substrates having a low activity ratio compared to parent cell lines.

DISCLOSURE OF THE INVENTION

The present invention was made considering the above circumstances. An objective of the present invention is to provide methods for measuring the target transporter activity, which have a low background level and a high degree of sensitivity. In addition, another objective of the present invention is to provide methods of screening for substances that inhibit or promote the transport activity of transporters, using the above methods.

Since viruses have no fundamental need to self-reproduce, the present inventors speculated that there was no physiological value in taking up substances essential to maintenance of life. Thus, they focused on the assumption that endogenous transporters may not be expressed (or may be expressed in extremely low amounts) on viral envelopes. The method for measuring transporter activity using budding baculoviruses that do not express endogenous transporters on their envelopes are thought to have a low background level, and to enable a highly sensitive measurement of target activity. Furthermore, by using such methods, functional changes due to transporter SNPs can be measured for a broader range of substrates, and may be applied to tailor-made therapies.

Specifically, the present invention provides:

[1] a method for expressing a transporter having transporter activity, wherein the method comprises culturing a host infected with a recombinant virus that comprises a gene encoding the transporter, and expressing the transporter on the envelope of a budding virus released from the host;

[2] the method of [1], wherein the virus is a baculovirus;

[3] the method of [1] or [2], wherein the transporter is of a non-viral origin;

[4] the method of any of [1] to [3], wherein the transporter is a peptide transporter or an organic anion transporter;

[5] the method of [4] wherein the transporter is PepT1, PepT2, or OATP-C;

[6] a virus that expresses a transporter having transporter activity;

[7] the virus of [6], wherein the transporter is of a non-viral origin;

[8] the virus of [7] wherein the virus is a baculovirus;

[9] the virus of any of [6] to [8] wherein the virus is a budding virus;

[10] the virus of any of [6] to [9] wherein the transporter is a peptide transporter or an organic anion transporter;

[11] the virus of [10] wherein the transporter is PepT1, PepT2, or OATP-C;

[12] a method for measuring the activity of a transporter, wherein the method comprises expressing the transporter on a viral envelope;

[13] the method of [12] wherein the virus is a budding baculovirus;

[14] the method of [12] or [13] wherein the transporter is a peptide transporter or an organic anion transporter;

[15] the method of [14] wherein the transporter is PepT1, PepT2, or OATP-C;

[16] a method of screening for a substance that inhibits or promotes transport activity of a transporter, wherein the method comprises the following steps:

(a) expressing the transporter on a viral envelope, (b) contacting the transporter with a test substance, and (c) selecting a substance that inhibits or promotes the transport activity;

[17] the method of [16] wherein the virus is a baculovirus;

[18] the method of [16] or [17] wherein the virus is a budding virus;

[19] the method of any of [16] to [18], wherein the transporter is of a non-viral origin;

[20] the method of any of [16] to [19], wherein the transporter is a peptide transporter or an organic anion transporter;

[21] the method of [20] wherein the transporter is PepT1, PepT2, or OATP-C;

[22] the method of any of [16] to [21], which comprises immobilizing the virus on a support;

[23] the method of [22] wherein the virus is immobilized on the support through an antibody against an envelope protein expressed on the viral envelope; and,

[24] the method of [22] wherein the virus is immobilized on the support through a biotin-streptavidin reaction by biotinylating a protein expressed on the viral envelope.

The present invention relates to methods for expressing transporters having transporter activity, which methods comprise culturing a host infected with a recombinant virus that comprises a gene coding for a transporter, and expressing the transporter on the envelope of a budding virus released from the host. Herein, examples of a "transporter" include peptide transporters, amino acid transporters, and sugar transporters. More specifically, transporters such as those listed in Table 1 can be given as examples.

TABLE 1

| Transporter | Driving force/ transport type | Amino acids | Trans-membrane | ncbi | Reference |
|---|---|---|---|---|---|
| 4F2hc | LAT regulatory factor | 529 | 1 | P08195 | Proc. Natl. Acad. Sci. U.S.A. 84 (18), 6526-6530 (1987) |
| AE4 | Cl/HCO exchange transport | 945 | 14 | AAK16733 | Commun. 282 (5), 1103-1109 (2001) |
| $ATB^0$/ASCT2 | Na/neutral amino acid cotransport | 541 | 10 | Q15758 | J. Biol. Chem. 271 (31), 18657-18661 (1996) |
| $ATB^{0+}$ | Na/neutral and basic amino acids cotransport | 642 | 12 | AAD49223 | J. Biol. Chem. 274 (34), 23740-23745 (1999) |
| BAT1/$b^{0+}$ AT | Facilitated diffusion (amino acid) | 487 | 12 | P82251 | Nat. Genet. 23 (1), 52-57 (1999) |
| BCRP | ATP/primary acive transport | 655 | 6 | AAC97367 | Proc. Natl. Acad. Sci. U.S.A. 95 (26), 15665-15670 (1998) |
| BSEP | ATP/primary active transport | 1321 | 12 | AAC77455 | Nat. Genet. 20 (3), 233-238 (1998) |
| BTR1 | Cl/HCO exchange transport | 891 | 14 | AAK16734 | Commun. 282 (5), 1103-1109 (2001) |
| CNT1 | Na/nucleoside cotransport | 649 | 13 | NP_004204 | Am. J. Physiol. 272 (2), C707-C714 (1997) |
| CNT2 | Na/nucleoside cotransport | 658 | 14 | O43868 | Am. J. Physiol. 273 (6 Pt 2), F1058-F1065 (1997) |
| CNT3 | Na/nucleoside cotransport | 691 | 13 | NP_071410 | J. Biol. Chem. 276 (4), 2914-2927 (2001) |
| DRA/CLD | Cl/HCO exchange transport | 764 | | P40879 | Proc. Natl. Acad. Sci. U.S.A. 90 (9), 4166-4170 (1993) |
| EAAC1 | Na/acidic amino acid cotransport | 525 | 12 | NP_004161 | Genomics 20 (2), 335-336 (1994) |
| ENT1 | Facilitated diffusion (nucleoside) | 456 | 14 | NP_004946 | Nat. Med. 3 (1), 89-93 (1997) |
| ENT2 | Facilitated diffusion (nucleoside) | 456 | 14 | AAC39526 | Biochem. J. 328 (Pt 3), 739-743 (1997) |
| FORT | Folic acid | 591 | 12 | P41440 | Commun. 206 (2), 681-687 (1995) |
| GAT1 | Na/GABA cotransport | 599 | 12 | NP_003033 | FEBS Lett. 269 (1), 181-184 (1990) |
| GAT3 | Na/GABA cotransport | 632 | 12 | P48066 | Recept. Channels 2 (3), 207-213 (1994) |
| GLUT1 | Facilitated diffusion (glucose) | 492 | 12 | NP_006507 | Science 229 (4717), 941-945 (1985) |

TABLE 1-continued

| Transporter | Driving force/ transport type | Amino acids | Trans-membrane | ncbi | Reference |
|---|---|---|---|---|---|
| GLUT2 | Facilitated diffusion (glucose) | 524 | 12 | NP_000331 | Proc. Natl. Acad. Sci. U.S.A. 85 (15), 5434-5438 (1988) |
| GLUT3 | Facilitated diffusion (glucose) | 496 | 12 | NP_008862 | J. Biol. Chem. 263, 15245-15248 (1988) |
| GLUT4 | Facilitated diffusion (glucose) | 509 | 12 | NP_001033 | J. Biol. Chem. 264 (14), 7776-7779 (1989) |
| GLVR1/PiT-1 | Na/Pi cotransport | 679 | 10 | NP_005406 | Cell Growth Differ. 1 (3), 119-127 (1990) |
| GLVR2/PiT-2 | Na/Pi cotransport | 652 | 10 | NP_006740 | J. Virol. 65 (11), 6316-6319 (1991) |
| LAT1 | Facilitated diffusion (amino acid) | 507 | 12 | JG0165 | Commun. 255 (2), 283-288 (1999) |
| LRP | ATP/primary active transport | 896 | | NP_059447 | Nat. Med. 1 (6), 578-582 (1995) |
| MCT1 | H/organic anion cotransport | 500 | 12 | NP_003042 | Genomics 23 (2), 500-503 (1994) |
| MCT2 | H/organic anion cotransport | 478 | 12 | O60669 | J. Biol. Chem. 273 (44), 28959-28965 (1998) |
| MCT3 | H/organic anion cotransport | 465 | 12 | O15427 | Biochem. J. 329 (Pt 2), 321-328 (1998) |
| MCT4 | H/organic anion cotransport | 487 | 12 | O15374 | Biochem. J. 329 (Pt 2), 321-328 (1998) |
| MCT5 | H/organic anion cotransport | 505 | 12 | O15375 | Biochem. J. 329 (Pt 2), 321-328 (1998) |
| MCT6 | H/organic anion cotransport | 523 | 12 | O15403 | Biochem. J. 329 (Pt 2), 321-328 (1998) |
| MDR1 | ATP/primary active transport | 1279 | 12 | AAB69423 | Cell 47 (3), 381-389 (1986) |
| MDR3 | ATP/primary active transport | 1279 | 12 | P21439 | EMBO J. 6 (11), 3325-3331 (1987) |
| MRP1 | ATP/primary active transport | 1531 | 17 | P33527 | Science 258 (5088), 1650-1654 (1992) |
| MRP2 | ATP/primary active transport | 1545 | 17 | Q92887 | Cancer Res. 56 (18), 4124-4129 (1996) |
| MRP3 | ATP/primary active transport | 1527 | 17 | NP_003777 | Cancer Res. 57 (16), 3537-3547 (1997) |
| MRP4 | ATP/primary active transport | 1325 | 12 | NP_005836 | Cancer Res. 57 (16), 3537-3547 (1997) |
| MRP5 | ATP/primary active transport | 1437 | 12 | O15440 | Cancer Res. 57 (16), 3537-3547 (1997) |
| MRP6 | ATP/primary active transport | 1503 | 17 | O95255 | Cancer Res. 59 (1), 175-182 (1999) |
| MRP7 | ATP/primary active transport | 1492 | 17 | | Cancer Lett. 162 (2), 181-191 (2001) |
| NaPi-3B | Na/Pi cotransport | 690 | 8 | NP_006415 | Commun. 258 (3), 578-582 (1999) |
| NaSi-1 | Na/Si cotransport | 595 | 13 | NP_071889 | Genomics 70 (3), 354-363 (2000) |
| NHE1 | Na/H exchange transport | 815 | 12 | P19634 | Cell 56 (2), 271-280 (1989) |
| NHE2 | Na/H exchange transport | 812 | 12 | NP_003039 | Am. J. Physiol. 40 (2), 383-390 (1999) |
| NHE3 | Na/H exchange transport | 834 | 12 | NP_004165 | Am. J. Physiol. 269 (1 Pt 1), C198-C206 (1995) |
| NPT1 | Na/Pi cotransport | 467 | 6-8 | Q14916 | Genomics 18 (2), 355-359 (1993) |
| NPT2/NaPi-3 | Na/Pi cotransport | 639 | 8 | NP_003043 | Proc. Natl. Acad. Sci. U.S.A. 90, 5979-5983 (1993) |
| Nramp2/DCT1 | Na/Fe cotransport | 568 | 12 | P49281 | Mol. Immunol. 34 (12-13), 839-842 (1997) |
| NTCP2/ASBT | Na/bile acid cotransport | 348 | 7 | NP000443 | J. Biol. Chem. 270 (45), 27228-27234 (1995) |
| OAT1 | Facilitated diffusion (organic anion) | 550 | 12 | NP_004781 | Commun. 255 (2), 508-514 (1999) |
| OAT2 | Facilitated diffusion (organic anion) | 548 | 12 | NP_006663 | |
| OAT3 | Facilitated diffusion (organic anion) | 568 | 12 | NP_004781 | Commun. 255 (2), 508-514 (1999) |
| OAT4 | Facilitated diffusion (organic anion) | 550 | 12 | AAK68155 | J. Biol. Chem. 275 (6), 4507-4512 (2000) |
| OATP-A | Facilitated diffusion (organic anion) | 670 | 12 | NP_066580 | Gastroenterology 109 (4), 1274-1282 (1995) |
| OATP-B | Facilitated diffusion (organic anion) | 709 | 12 | NP_009187 | Commun. 273 (1), 251-260 (2000) |
| OATP-C | Facilitated diffusion (organic anion) | 691 | 12 | BAA78639 | Commun. 273 (1), 251-260 (2000) |

TABLE 1-continued

| Transporter | Driving force/ transport type | Amino acids | Trans-membrane | ncbi | Reference |
|---|---|---|---|---|---|
| OATP-D | Facilitated diffusion (organic anion) | 710 | 12 | BAA89287 | Commun. 273 (1), 251-260 (2000) |
| OATP-E | Facilitated diffusion (organic anion) | 722 | 12 | BAA89288 | Commun. 273 (1), 251-260 (2000) |
| OCT1 | Facilitated diffusion (organic cation) | 554 | 12 | NP_003048 | Mol. Pharmacol. 51 (6), 913-921 (1997) |
| OCT2 | Facilitated diffusion (organic cation) | 555 | 12 | NP_003049 | DNA Cell Biol. 16 (7), 871-881 (1997) |
| OCT3 | Facilitated diffusion (organic cation) | 551 | 12 | NP_035525 | Genomics 55 (2), 209-218 (1999) |
| OCTN1 | H/organic cation | 551 | 11 | NP_003050 | FEBS Lett. 419 (1), 107-111 (1997) |
| OCTN2 | Na/organic cation cotransport | 557 | 12 | O76082 | Commun. 246 (3), 589-595 (1998) |
| PGT | Facilitated diffusion (organic anion) | 643 | 12 | NP_005612 | Commun. 221 (2), 454-458 (1996) |
| rBAT | BAT1 regulatory factor | 685 | 1 | AAA81778 | J. Biol. Chem. 268 (20), 14842-14849 (1993) |
| SDCT1/NaDC-1 | Na/dicarboxylic acid cotransport | 592 | 8 | NP_003975 | Am. J. Physiol. 270 (4 Pt 2), F642-F648 (1996) |
| SGLT1 | Na/glucose cotransport | 664 | 14 | NP00334 | Proc. Natl. Acad. Sci. U.S.A. 86 (15), 5748-5752 (1989) |
| SGLT2 | Na/glucose cotransport | 672 | 14 | NP_003032 | Am. J. Physiol. 263 (3 Pt 2), F459-F465 (1992) |
| SGLT3/SAAT1 | Na/glucose cotransport | 659 | 14 | P31636 | J. Biol. Chem. 268 (3), 1509-1512 (1993) |
| SLC26A6 | Cl/HCO exchange transport | 738 | 11 | NP_075062 | Genomics 70 (1), 102-112 (2000) |
| SVCT1 | Na/vitamin C cotransport | 598 | 12 | NP_005838 | Biochim. Biophys. Acta 1461 (1), 1-9 (1999) |
| UT2 | Urea (Facilitated diffusion) | 397 | 10 | Q15849 | FEBS Lett. 386 (2-3), 156-160 (1996) |

Preferable transporters in the present invention are peptide transporters or organic anion transporters, and especially preferable are PepT1, Pept2, and OATP-C. The nucleotide and amino acid sequences of PepT1 and PepT2 are known (human PepT1: GenBankXM_007063, J. Biol. Chem. 270 (12): 6456-6463 (1995); human PepT2: GenBank NP_066568, XM_002922, Biochem. Biophys. Acta. 1235: 461-466 (1995); mouse PepT1 GenBankAF205540, Biochim. Biophys. Acta. 1492: 145-154 (2000); mouse PepT2: GenBankNM_021301, Biochim. Biophys. Res. Commun. 276: 734-741 (2000)). Furthermore, the nucleotide and amino acid sequence of OATP-C are also known (Table 1: Commun. 273(1), 251-260 (2000)). However, the transporters of the present invention are not particularly limited thereto, as long as they can be expressed on a viral envelope.

Genes encoding the transporters, for example, those listed in Table 1, are registered with the National Centre for Biotechnology Information (NCBI) under the listed accession numbers. For example, based on this sequence information, cDNA libraries or genomic libraries can be screened to obtain genes coding for transporters. More specifically, for example, cDNA or genomic libraries are screened using probes (antibodies against target transporters, or oligonucleotides that hybridise to nucleotide sequences coding for target transporters). Screening can be carried out, for example, by following the standard methods described by Sambrook et al. in Chapters 10 to 12 of "Molecular Cloning: A Laboratory Manual" (New York, Cold Spring Harbor Laboratory Press, 1989). Alternatively, genes encoding target transporters can be isolated using PCR (see e.g., Chapter 14 in the above-mentioned Sambrook et al., 1989).

As methods for expressing transporters on viral envelopes, for example, the method of WO98/46777 or Loisel et al. for expressing envelope proteins using budding baculoviruses can be used (Loisel, T. P. et al., Nature Biotech. 15: 1300-1304 (1997)). More specifically, a recombinant vector for insect cells comprising a gene encoding a transporter is constructed, and inserted, along with baculoviral DNA, into insect cells such as Sf9. The transporter encoded by the recombinant vector is then expressed on mature viral particles (virions), which are released by infected cells to the outside of cells prior to infected cell death. Thus recombinant viruses that express the transporter can be obtained.

In the present invention, a budding virus is a virus that is released from infected cells by budding. Generally, viruses covered by an envelope can bud from cells infected with these viruses, even when the cells have not been destroyed, and are released continuously. On the other hand, adenoviruses that are not covered by an envelope, and herpes viruses that are covered by a nuclear envelope, are released from the cells all at once upon their destruction. In the present invention, budding viruses are particularly preferable. In addition, hosts infected with a recombinant virus in the present invention can be suitably selected by those skilled in the art, depending on the type of virus used, so long as viral replication is possible in the host. For example, insect Sf9 cells can be used when using baculoviruses. Generally, protein expression systems using baculoviruses and insect cells may be useful because modifications such as fatty acid acetylation or glycosylation are carried out at the same time as translation or post-translation, in the same way as in mammalian cells. In addition, the expression level of heterologous proteins in such systems is greater than that in mammalian cell systems (Luckow V. A. and Summers M. D., Virol. 167: 56 (1988)).

The present invention also provides viruses that express transporters comprising transporter activity. Examples of these viruses include baculoviruses, papillomaviruses, polyomaviruses, simian virus 40 (SV40), adenoviruses, Epstein-Bar virus (EBV), and retroviruses. In the present invention, particularly preferable viruses include the AcMNPV (Invitrogen) baculovirus, and budding viruses. In addition, the transporters expressed by the viruses are preferably of a non-viral origin, for example the transporters in Table 1. Of these, peptide transporters and organic anion transporters are preferable, and Pept 1, PepT2, and OATP-C are even more preferable.

The viruses expressing transporters having transporter activity of the present invention can be obtained by, for example, culturing a host that has been infected with a recombinant virus comprising a gene that codes for a transporter. Alternatively, using methods such as the above-mentioned methods of WO98/46777 and Loisel et al (Loisel, T. P. et al., Nature Biotech. 15: 1300-1304 (1997)), a recombinant vector encoding a transporter can be inserted into an insect cell along with a baculovirus, and transporters can be expressed on the envelope of the baculovirus which is released outside of the cell. In addition, using methods like that of Strehlow et al. (D. Strehlow et al., Proc. Natl. Acad. Sci. USA. 97:4209-4214 (2000)), packaging cells such as PA317 can be infected with recombinant Moloney murine leukemia viruses, which are constructed using vectors derived from Moloney viruses introduced with transporter-encoding genes, and the transporters can be expressed on the envelope of the viruses released outside of the cells. However, the viruses of the present invention that express transporters having transporter activity are not limited to those that are constructed using the above methods. They include viruses constructed using any method as long as transporters can be expressed in viral particles or on viral surfaces.

Recombinant viruses constructed as described above can be purified using known methods. For example, known methods for purifying viruses include: augmented density gradient centrifugation (Albrechtsen et al., J. Virological Methods 28: 245-256(1990); Hewish et al., J. Virological Methods 7: 223-228 (1983)), size exclusion chromatography (Hjorth and Mereno-Lopez, J. Virological Methods 5: 151-158 (1982); Crooks et al., J. Chrom. 502: 59-68 (1990); Mento S. J. (Viagene, Inc.) 1994 Williamsburg Bioprocessing Conference), affinity chromatography using monoclonal antibodies, sulphated fucose-containing polysaccharides and the like (Najayou et al., J. Virological Methods 32: 67-77 (1991); Diaco et al., J. Gen. Virol. 67: 345-351 (1986); Fowler, J. Virological Methods 11: 59-74 (1986); TOKUSAIHYOU No. 97/032010 (Unexamined Publication of Japanese National Phase Patent Application)), and DEAE ion exchange chromatography (Haruna et al., Virology 13: 264-267 (1961)). Viruses that express transporters of the present invention are not limited to these, and can be purified using the above methods, or combinations thereof.

The present invention relates to methods for measuring the activity of transporters, which comprise expressing transporters on viral envelopes. For example, measurement of transporter activity using budding baculoviruses can be carried out by the following method. First, if necessary, a substrate to be taken into the virus by the transporters is labelled so as to be detected. For example, the substrate is labelled with radioactive substances, fluorescence, or so on. Next, the substrate is mixed with the budding baculovirus that expresses the transporter, and reacted at 37° C. After a set length of time, the reaction solution is transferred onto a filter such as a cellulose membrane. The substrate taken into the virus is separated by vacuum filtration from the substrate that was not taken up. The filter is washed several times using an ice-cold buffer, and the substrate concentration in the viruses which are trapped on the filter is determined using a liquid scintillation counter, a fluorescence detector, HPLC, or such. Nonspecific uptake can be detected by the substrate uptake into wild type viruses that do not express the transporter. In addition, nonspecific uptake can also be evaluated by carrying out experiments on substrate uptake by coexisting the substrate with transporter inhibitors, or if the substrate is radioactive, by coexisting it with an excess of unlabelled substance. Non-specific uptake can be evaluated by carrying out uptake experiments at 4° C.

As an alternative method, budding baculovirus solutions expressing a transporter can be added to a 96-well plate and incubated overnight at 4° C. to perform plate coating. Alternatively, antibodies against proteins such as gp64 protein, which is highly expressed on viral envelopes, can be added to a 96-well plate, and incubated overnight at 4° C. After this, budding baculoviruses that express the transporter are added to the plate. Antibodies against membrane proteins, such as anti-gp64 antibodies (Novagen, Clontech), can also be used to coat the plate with the viruses. A substrate is then added to the plate, and reaction begins. After a set time, the plate is washed with ice-cold buffer, and substrates that were not taken up by the viruses are removed. The amount of substrates taken up into the virus is measured using a liquid scintillation counter, fluorescence detector, HPLC, or so on. If non-specific adsorption is high, blocking can be carried out prior to measuring activity, using skim milk or such. Non-specific uptake can be detected by substrate uptake into wild-type viruses not expressing the transporter. In addition, transporter inhibitors can be coexisted with the substrate to detect non-specific uptake. Alternatively, when the substrate is a radioactive substance, non-specific uptake can also be evaluated by carrying out uptake experiments by coexisting the substrate with an excess of unlabeled substances. Furthermore, uptake experiments can be carried out at 4° C. to evaluate non-specific uptake.

Usually, cell membrane vesicles prepared from biological resources, cultured cells, and such are preserved in a deep freezer or in liquid nitrogen. However, budding baculoviruses can be preserved at 4° C., and do not require any special freezing devices. In addition, there are no complicated steps such as cell culturing, and there is no requirement for special equipment when measuring activity, as used in electrophysiological methods. Thus, budding baculovirus expression systems are simple methods for measuring transporter activity.

The methods of the present invention for measuring the transporter activity that comprise expressing transporters on viral envelopes can also be applied in searching for substances that inhibit or promote the transporter activity. In particular, methods using budding baculovirus expression systems are simple, and useful in identifying substances that inhibit or promote the transporter activity. Specifically, the methods of the present inventions produce, for example, budding baculoviruses that express target transporters. The radioactive or fluorescent substrates of those transporters are mixed with test substances, and added to the transporter-expressing viruses. Before adding the substrates, compounds can be preloaded to the viruses. Transport activity in the absence of a test substrate is taken as 100, and substances that inhibit or promote the transporter activity are searched for by using changes in activity in the presence of the test substrate as an index. Whether or not the test compound is inhibiting or promoting the transporter activity can be judged by known methods, for example, by labeling the transport target substrate (e.g. peptides in the case of peptide transporters) with a radioactive substance (such as $^{14}C$) or fluorescent substance, and then measuring the amount of that substrate that is taken up by a transporter-expressing virus, etc.

Examples of test substances in the methods of screening for substances that inhibit or promote transport activity of the transporters of the present invention include, but are not limited to, purified or crude proteins (comprising antibodies), gene library expression products, synthetic peptide libraries, cell extracts, cultured cell supernatants, products of fermentation microorganisms, marine organism extracts, vegetable extracts, synthetic low molecular weight compound libraries, peptides, non-peptide compounds, and natural compounds.

Transporters expressed on viral envelopes can be contacted with test compounds in the form of, for example, a purified protein, a form bound to a carrier, a fusion protein with another protein, or a membrane fraction. Herein, examples of carriers on which viruses can be immobilized include synthetic or natural organic high molecular weight compounds, inorganic materials such as glass beads, silica gel, alumina, and active carbon, and these materials coated with polysaccharides or synthetic high molecular weight molecules. Examples of organic high molecular weight compounds comprise a large number of compounds, including polysaccharides such as agarose, cellulose, chitin, chitosan, sepharose, and dextran, polyesters, polyvinyl cholorides, polystyrenes, polysulfones, polyether sulphones, polypropylenes, polyvinyl alcohols, polyamides, silicon resins, fluorocarbon resins, polyurethanes, polyacrylamides, and derivatives thereof. However, so long as the viruses can be immobilized, it is understood that the compositions of the compounds are not especially limited. The form of the carrier is also not particularly limited, and examples include membranes such as a plate, fibers, granules, hollow filaments, nonwoven fabrics, porous forms, and honeycomb forms. However, in the present invention, simplicity of immobilization makes commercially available plates especially preferable. By changing the form, surface area and such of these carriers, the contact area of test compounds can be controlled. Viruses can be immobilized to carriers using, for example, antibodies against the envelope proteins expressed in the viruses. In addition, immobilization onto carriers can also be achieved using streptoavidin, avidin or such when biotinylated beforehand.

The physiological function of transporters can be elucidated by searching for inhibitors or promoters of transporter activity. At the same time, those inhibitors or promoters may be applied to developing pharmaceutical agents for diseases caused by transporter abnormalities.

The present invention's budding baculoviruses that express promoters, and the envelope portions that comprise a transporter of those viruses, can be used as screening antigens or immune antigens when producing transporter antibodies. Preparation of such an antigen can be carried out, for example, according to the methods using baculoviruses described in WO98/46777.

Conventionally, in the construction of anti-transporter antibodies, it was problematic to use an active transporter as an immunogen. However, transporters that are expressed by the methods of the present invention have been confirmed to have transporter activity. Thus, an active transporter can be used as an immunogen by using the present invention's transporter-expressing viruses, or envelope portions that comprise a transporter of those viruses.

Therefore, it is extremely useful to construct antibodies using, as immunogens, the present invention's transporter-expressing viruses and envelope portions that comprise a transporter of those viruses.

Thus, the present invention provides methods for constructing anti-transporter antibodies, which methods comprise using, as immunogens, the present invention's transporter-expressing viruses or envelope portions that comprise a transporter of those viruses. The present invention also provides the antibodies constructed using these methods.

Transporter antibodies of the present invention can be constructed by those skilled in the art, using known methods where non-human animals are administered, by subcutaneous or intraperitoneal injection, several times with transporter-expressing viruses or envelope portions that comprise a transporter of those viruses.

The mammals immunized with sensitizing antigens are not particularly limited, however are preferably selected considering compatibility with parent cells used for cell fusion. Animals generally used include rodents, lagomorphs, and primates.

Examples of rodents that can be used are mice, rats, and hamsters. As lagomorphs, for example, rabbits can be used. Examples of primates are monkeys. Monkeys that can be used include catarrhines (old-world monkeys) such as cynomolgous monkeys, rhesus monkeys, hamadryas, and chimpanzees.

Animals can be immunized with a sensitizing antigen using known methods. General methods include injecting a sensitizing antigen into a mammal by subcutaneous or intraperitoneal injection. Specifically, a sensitizing antigen is diluted with an appropriate volume of Phosphate-Buffered Saline (PBS) or physiological saline, and if desired, the suspension is mixed with an appropriate volume of a conventional adjuvant, for example, Freund's complete adjuvant. After emulsification, this is applied to the mammals. In addition, after this, the sensitizing antigen that has been mixed with an appropriate volume of Freund's incomplete adjuvant is preferably applied every four to 21 days for several times. When immunizing a sensitizing antigen, an appropriate carrier can also be used. Thus immunization occurs, and the increased level of the desired antibody in the serum can be confirmed using conventional methods.

Herein, in obtaining the polyclonal antibodies against the transporters of the present invention, the increase in the level of the desired antibody in the serum is confirmed, and blood is then obtained from the mammals sensitized to the antigens. Serum can be separated from this blood using known methods. As polyclonal antibodies, serum comprising polyclonal antibodies can be used. Where necessary, fractions comprising polyclonal antibodies can be isolated from this serum, and this fraction can also be used. For example, fractions that only recognize the transporters of the present invention can be obtained using affinity columns coupled to these transporters. By purifying these fractions using a protein A or protein G column, immunoglobulin G or M can be prepared.

In obtaining monoclonal antibodies, the increased level of the desired antibody is confirmed in the mammals sensitized to the above antigen, immunocytes can be obtained from the mammals, and then subjected to cell fusion. In this case, immunocytes for cell fusion can preferably be splenocytes. As the parent cells to which the above-mentioned immunocytes are bound, mammal myeloma cells are preferable, and more preferable are myeloma cells that have acquired a characteristic for selection of fusion cells using a pharmaceutical agent.

The above-mentioned cell fusion of immunocytes and myeloma cells can be performed according to known methods, for example, the method of Milstein et al. (Galfre, G. and Milstein, C., Methods Enzymol. (1981) 73, 3-46).

Hybridomas obtained from the cell fusions can be selected by culturing in a conventional selective culture medium, for example HAT culture medium (medium comprising hypoxanthine, aminopterin, and thymidine). Culture in this HAT culture medium is carried out for a continuous period of usually several days to several weeks, a sufficient time to kill cells other than the target hybridomas (non-fusion cells). Next, conventional limiting dilution methods are carried out, and hybridomas that produce the target antibodies are screened and cloned.

In addition to obtaining the above-mentioned hybridomas by immunizing non-human animals with an antigen, human lymphocytes, for example human lymphocytes infected with EB virus, are sensitized in vitro to a virus expressing a transporter of the present invention, or to an envelope portion comprising a transporter of that virus. The sensitized lymphocytes are fused with human-derived myeloma cells that can permanently divide, for example U266. Thus, hybridomas that produce the desired human antibodies that have the activity to bind to the transporters can be obtained (Unexamined Published Japanese Patent Application No. (JP-A) Sho 63-17688).

The obtained hybridomas are transplanted into mice peritoneal cavities, and ascites are recovered from the mice. The monoclonal antibodies thus obtained can be prepared by purification using ammonium sulphate precipitation, protein A or G columns, DEAE ion exchange chromatography, affinity columns to which a transporter of the present invention has been coupled, or the like. In addition to being used for the purification and detection of the transporters of the present invention, the antibodies of the present invention can become candidates for agonists and antagonists of these transporters. Furthermore, these antibodies can also be applied to antibody therapies for diseases involving transporters of the present invention. When using the obtained antibodies for the purpose of application to the human body (antibody therapy), human antibodies and humanized antibodies are preferable due to their low antigenicity.

For example, antibody-producing cells can be obtained by immunizing transgenic animals that comprise a repertoire of human antibody genes, with a virus expressing a transporter that becomes the antigen, or a portion of the viral envelope comprising the transporter. Hybridomas produced by fusing the antibody-producing cells with myeloma cells can be used to obtain human antibodies against the transporter (see International Publication WO92-03918, WO93-2227, WO94-02602, WO94-25585, WO96-33735, and WO96-34096).

In addition to producing antibodies by using hybridomas, immunocytes of antibody-producing sensitized lymphocytes and such that have been immortalized using oncogenes can also be used.

Monoclonal antibodies obtained in this way can also be obtained as recombinant antibodies produced using gene recombination technologies (for example, see Borrebaeck, C. A. K. and Larrick, J. W., Therapeutic Monoclonal Antibodies, UK, Macmillan Publishers Ltd., 1990). Recombinant antibodies can be produced by cloning DNA that encodes them from immunocytes such as hybridomas and antibody-producing sensitized lymphocytes, incorporating into a suitable vector, and introducing this into a host. The present invention also encompasses such recombinant antibodies.

So long as the antibodies of the present invention bind to the polypeptides of the present invention, they can also be antibody fragments, modified antibodies, etc. For example, an antibody fragment can be an Fab, F(ab')2, Fv, or a single chain Fv (scFv) where Fvs of H chain and L chain are linked by a suitable linker (Huston, J. S. et al., Proc. Natl. Acad. Sci. U.S.A., (1998) 85, 5879-5883). Specifically, the antibody fragments can be produced by treating antibodies with an enzyme such as papain or pepsin. Alternatively, genes encoding these antibody fragments are constructed, inserted into an expression vector, and expressed in appropriate host cells (see for example, Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Antibodies bound to various molecules such as polyethylene glycols (PEG), can also be used as the modified antibodies. "Antibody" in the present invention also encompasses these modified antibodies. Such a modified antibody can be obtained by chemically modifying obtained antibodies. These methods have already been established in the art.

By using known technologies, the antibodies of the present invention can be obtained as chimeric antibodies comprising non-human antibody-derived variable regions and human antibody-derived constant regions, or alternatively, as humanized antibodies comprising non-human antibody-derived complementarity determining regions (CDRs), human antibody-derived framework regions (FRs), and constant regions.

Antibodies obtained as above can be purified until homogenous. The separation and purification of antibodies used in the present invention can use conventional separation and purification methods. For example and without limitation, antibodies can be separated and purified by appropriately selecting and combining chromatography columns such as affinity chromatography columns, filters, ultrafiltration, salt precipitation, dialysis, SDS polyacrylamide gel electrophoresis, isoelectric focusing and so on (Antibodies: A Laboratory Manual. Ed Harlow and David Lane, Cold Spring Harbor Laboratory, 1988). The concentration of the above-obtained antibodies can be determined by measuring absorbance, by enzyme-linked immunosorbent assays (ELISA), etc.

Protein A columns, protein G columns, and such can be used as the columns used for affinity chromatography. For example, as the columns using protein A, Hyper D, POROS, Sepharose F.F. (Pharmacia) and so on can be used.

Examples of chromatography other than affinity chromatography include ion exchange chromatography, hydrophobic chromatography, gel filtration, reverse chromatography, and adsorption chromatography (Strategies for Protein Purification and Characterisation: A Laboratory Course Manual. Ed Daniel R, Marshak et al., Cold Spring Harbor Laboratory Press, 1996). These chromatographies can be carried out using liquid phase chromatography such as HPLC and FPLC.

Examples of the methods for measuring antigen-binding activities of the antibodies of the present invention include absorbance measurements, enzyme-linked immunosorbent assays (ELISA), enzyme immunoassays (EIA), radioimmunoassay (RIA), and immunofluorescence. When using ELISA, the transporters of the present invention are added to a plate to which the antibodies of the present invention have been solid phased. Next, samples comprising a target antibody, for example the culture supernatant of antibody-producing cells or purified antibodies, are added. Secondary antibodies that recognise the antibody, which is labelled with enzymes such as alkaline phosphatase, are then added and the plate is incubated. After washing, an enzyme substrate such as p-nitrophenol phosphate is added, and antigen-binding activity can be evaluated by measuring absorbance. BIAcore (Pharmacia) can be used to evaluate the activity of the antibodies of the present invention.

Transporter-binding antibodies can be screened by ELISA using 96-well plates coated with budding baculoviruses.

Antibodies against the viral antigens can be removed by ELISA using wild type viruses as the screening antigen. Alternatively, hybridoma culture supernatant and a wild type virus can be reacted, and after antibodies against the viral antigen have been removed, ELISA can be then carried out using a transporter-expressing virus as the screening antigen to acquire transporter-binding antibodies. Function-inhibiting antibodies can also be screened for from the binding antibodies. In other words, a radioactive or fluorescent substrate of the target transporter can be mixed with a solution comprising antibodies, such as hybridoma culture supernatant, and then added to a transporter-expressing virus. The solution comprising antibodies, such as hybridoma culture supernatant, can be preloaded onto the virus prior to adding the substrate. Transport activity in the absence of antibodies is taken as 100, and function-inhibiting antibodies can be screened for using, as an index, decreased activity in the presence of antibodies. Transporter topography at the cellular level can be revealed by binding antibodies to that transporter. In addition, function-inhibiting antibodies can be added to cell cultures or administered to laboratory animals to make a great contribution to the elucidation of the physiological functions of the transporters. Function-inhibiting antibodies or binding antibodies to transporters associated with disease can be applied as pharmaceutical agents.

The present invention can also be used to evaluate the ways in which transporter activity is altered by changes in amino acid sequence due to mutations, polymorphisms such as SNPs, and so on. For example, many SNPs exist in OATP-Cs, and changes in the amino acid sequence due to these SNPs have been reported (J. Biol. Chem., 276 (2001). By using the methods of the present invention to measure the transport activity of each of these OATP-Cs with altered amino acid sequences, the SNPs that influence transport activity can be identified, transporters with high activity can be screened, and so on.

In addition, after mutants have been created by artificial substitution, insertion, deletion, or addition of transporter amino acid sequences, transporter activity can be measured and transporters with high activity can be screened, or regions that influence transporter activity can be identified. Those skilled in the art can prepare transporters with substituted amino acids by using well-known methods. For example, site-specific mutagenesis and such can be used (Hashimoto-Gotoh, T. et al., Gene, 152, 271-275, (1995); Zoller, M J, and Smith, M., Methods Enzymol, 100, 468-500, (1983); Kramer, W et al., Nucleic Acids Res, 12, 9441-9456, (1984); Kramer, W and Fritz, H J., Method Enzymol, 154, 350-367, (1987); Kunkel, T A., Proc Natl Acad Sci USA, 82, 488-492, (1985); Kunkel, T A., Methods Enzymol, 85, 2763-2766, (1988)).

Further, when using the present invention, substances transported by a transporter can be used as test substances and measure transporter activity to screen for substances that are easily transported by transporters, or substances that are difficult to transport.

The present invention can also be applied to proteins other than transporters. For example, similar methods for measuring activity, screening and such can be carried out for ion channels such as sodium channels, calcium channels, potassium channels, chloride channels, cation channels, and anion channels. In this case, instead of a transporter, a channel is expressed on the viral envelope, and a substance passed through the channel can be used as a substrate. Channels that can be used in the present invention include those listed in Table 2. Thus, the present invention can be used for proteins that can transport or transmit a substance, such as transporters and ion channels (especially proteins which are expressed on membranes and can be transported or passed in a substrate-specific manner).

In addition to the above transporters and ion channels, the present invention can also be applied to G protein coupled receptors (GPCRs).

TABLE 2

| Symbol | Name | Sequence ID |
|---|---|---|
| ACCN1 | amiloride-sensitive cation channel 1, neuronal (degenerin) | NM_001094 |
| ACCN2 | amiloride-sensitive cation channel 2, neuronal | NM_001095<br>NM_020039 |
| ACCN3 | amiloride-sensitive cation channel 3, testis | NM_004769<br>NM_020321<br>NM_020322 |
| AQP1 | aquaporin 1 (channel-forming integral protein, 28 kD) | NM_000385 |
| ASIC4 | putative acid-sensing ion channel | NM_018674 |
| CACNA1A | calcium channel, voltage-dependent, P/Q type, alpha 1A subunit | NM_000068<br>NM_023035 |
| CACNA1B | calcium channel, voltage-dependent, L type, alpha 1B subunit | NM_000718 |
| CACNA1C | calcium channel, voltage-dependent, L type, alpha 1C subunit | NM_000719 |
| CACNA1D | calcium channel, voltage-dependent, L type, alpha 1D subunit | NM_000720 |
| CACNA1E | calcium channel, voltage-dependent, alpha 1E subunit | NM_000721 |
| CACNA1F | calcium channel, voltage-dependent, alpha 1F subunit | NM_005183 |
| CACNA1G | calcium channel, voltage-dependent, alpha 1G subunit | NM_018896 |
| CACNA1H | calcium channel, voltage-dependent, alpha 1H subunit | NM_021098 |
| CACNA1I | calcium channel, voltage-dependent, alpha 1I subunit | NM_021096 |
| CACNA1S | calcium channel, voltage-dependent, L type, alpha 1S subunit | NM_000069 |

TABLE 2-continued

| Symbol | Name | Sequence ID |
|---|---|---|
| CACNA2D | calcium channel, voltage-dependent, alpha 2/delta subunit 1 | NM_000722 |
| CACNA2D | calcium channel, voltage-dependent, alpha 2/delta subunit 2 | NM_006030 |
| CACNB1 | calcium channel, voltage-dependent, beta 1 subunit | NM_000723 |
| CACNB2 | calcium channel, voltage-dependent, beta 2 subunit | NM_000724 |
| CACNB3 | calcium channel, voltage-dependent, beta 3 subunit | NM_000725 |
| CACNB4 | calcium channel, voltage-dependent, beta 4 subunit | NM_000726 |
| CACNG1 | calcium channel, voltage-dependent, gamma subunit 1 | NM_000727 |
| CACNG2 | calcium channel, voltage-dependent, gamma subunit 2 | NM_006078 |
| CACNG3 | calcium channel, voltage-dependent, gamma subunit 3 | NM_006539 |
| CACNG4 | calcium channel, voltage-dependent, gamma subunit 4 | NM_014405 |
| CACNG5 | calcium channel, voltage-dependent, gamma subunit 5 | NM_014404 |
| CACNG6 | calcium channel, voltage-dependent, gamma subunit 6 | NM_031897 |
| CACNG7 | calcium channel, voltage-dependent, gamma subunit 7 | NM_031896 |
| CACNG8 | calcium channel, voltage-dependent, gamma subunit 8 | AF288388 |
| CLCA1 | chloride channel, calcium activated, family member 1 | NM_001285 |
| CLCA2 | chloride channel, calcium activated, family member 2 | NM_006536 |
| CLCA3 | chloride channel, calcium activated, family member 3 | NM_004921 |
| CLCA4 | chloride channel, calcium activated, family member 4 | NM_012128 |
| CLCN1 | chloride channel 1, skeletal muscle (Thomsen disease, autosomal dominant) | NM_000083 |
| CLCN2 | chloride channel 2 | NM_004366 |
| CLCN3 | chloride channel 3 | NM_001829 |
| CLCN4 | chloride channel 4 | NM_001830 |
| CLCN5 | chloride channel 5 (nephrolithiasis 2, X-linked, Dent disease) | NM_000084 |
| CLCN6 | chloride channel 6 | NM_001286<br>NM_021735<br>NM_021736<br>NM_021737 |
| CLCN7 | chloride channel 7 | NM_001287 |
| CLCNKA | chloride channel Ka | NM_004070 |
| CLCNKB | chloride channel Kb | NM_000085 |
| CLIC1 | chloride intracellular channel 1 | NM_001288<br>NM_001288 |
| CLIC2 | chloride intracellular channel 2 | NM_001289 |
| CLIC3 | chloride intracellular channel 3 | NM_004669 |
| CLIC4 | chloride intracellular channel 4 | NM_013943 |
| CLIC5 | chloride intracellular channel 5 | NM_016929 |
| CLIC6 | chloride intracellular channel 6 | BG184920 |
| CLNS1A | chloride channel, nucleotide-sensitive, 1A | NM_001293 |
| CNGA1 | cyclic nucleotide gated channel alpha 1 | NM_000087 |
| CNGA3 | cyclic nucleotide gated channel alpha 3 | NM_001298 |
| CNGB1 | cyclic nucleotide gated channel beta 1 | NM_001297 |
| CNGB3 | cyclic nucleotide gated channel beta 3 | NM_019098 |
| DKFZP43 | potassium channel modulatory factor | NM_020122 |
| ECAC1 | epithelial calcium channel 1 | NM_019841 |
| ECAC2 | epithelial calcium channel 2 | AJ243501<br>AJ243500 |
| HCN2 | hyperpolarization activated cyclic nucleotide-gated potassium channel 2 | NM_001194 |
| HCN4 | hyperpolarization activated cyclic nucleotide-gated potassium channel 4 | NM_005477 |
| HSA24339 | voltage-gated sodium channel beta-3 subunit (scn3b gene) | NM_018400 |
| HSA27226 | calcium channel, voltage-dependent, alpha 2/delta 3 subunit | NM_018398 |
| KCNA1 | potassium voltage-gated channel, shaker-related subfamily, member 1 (episodic ataxia with myokymia) | NM_000217 |

TABLE 2-continued

| Symbol | Name | Sequence ID |
|---|---|---|
| KCNA10 | potassium voltage-gated channel, shaker-related subfamily, member 10 | NM_005549 |
| KCNA2 | potassium voltage-gated channel, shaker-related subfamily, member 2 | NM_004974 |
| KCNA3 | potassium voltage-gated channel, shaker-related subfamily, member 3 | NM_002232 |
| KCNA4 | potassium voltage-gated channel, shaker-related subfamily, member 4 | NM_002233 |
| KCNA5 | potassium voltage-gated channel, shaker-related subfamily, member 5 | NM_002234 |
| KCNA6 | potassium voltage-gated channel, shaker-related subfamily, member 6 | NM_002235 |
| KCNA7 | potassium voltage-gated channel, shaker-related subfamily, member 7 | NM_031886 |
| KCNAB1 | potassium voltage-gated channel, shaker-related subfamily, beta member 1 | NM_003471 |
| KCNAB2 | potassium voltage-gated channel, shaker-related subfamily, beta member 2 | NM_003636 |
| KCNAB3 | potassium voltage-gated channel, shaker-related subfamily, beta member 3 | NM_004732 |
| KCNB1 | potassium voltage-gated channel, Shab-related subfamily, member 1 | NM_004975 |
| KCNB2 | potassium voltage-gated channel, Shab-related subfamily, member 2 | NM_004770 |
| KCNC1 | potassium voltage-gated channel, Shaw-related subfamily, member 1 | NM_004976 |
| KCNC3 | potassium voltage-gated channel, Shaw-related subfamily, member 3 | NM_004977 |
| KCNC4 | potassium voltage-gated channel, Shaw-related subfamily, member 4 | NM_004978 |
| KCND1 | potassium voltage-gated channel, Shal-related subfamily, member 1 | NM_004979 |
| KCND2 | potassium voltage-gated channel, Shal-related subfamily, member 2 | NM_012281 |
| KCND3 | potassium voltage-gated channel, Shal-related subfamily, member 3 | NM_004980 |
| KCNE1 | potassium voltage-gated channel, Isk-related family, member 1 | NM_000219 |
| KCNE1L | potassium voltage-gated channel, Isk-related family, member 1-like | NM_012282 |
| KCNE2 | potassium voltage-gated channel, Isk-related family, member 2 | NM_005136 |
| KCNE3 | potassium voltage-gated channel, Isk-related family, member 3 | NM_005472 |
| KCNF1 | potassium voltage-gated channel, subfamily F, member 1 | NM_002236 |
| KCNG1 | potassium voltage-gated channel, subfamily G, member 1 | NM_002237 |
| KCNG2 | potassium voltage-gated channel, subfamily G, member 2 | NM_012283 |
| KCNH1 | potassium voltage-gated channel, subfamily H (eag-related), member 1 | NM_002238 |
| KCNH2 | potassium voltage-gated channel, subfamily H (eag-related), member 2 | NM_000238 |
| KCNH3 | potassium voltage-gated channel, subfamily H (eag-related), member 3 | AB033108 |
| KCNH4 | potassium voltage-gated channel, subfamily H (eag-related), member 4 | NM_012285 |
| KCNH5 | potassium voltage-gated channel, subfamily H (eag-related), member 5 | U69185 |
| KCNIP1 | Kv channel-interacting protein 1 | NM_014592 |
| KCNIP2 | Kv channel-interacting protein 2 | NM_014591 |
| KCNJ1 | potassium inwardly-rectifying channel, subfamily J, member 1 | NM_000220 |
| KCNJ10 | potassium inwardly-rectifying channel, subfamily J, member 10 | NM_002241 |
| KCNJ11 | potassium inwardly-rectifying channel, subfamily J, member 11 | NM_000525 |
| KCNJ12 | potassium inwardly-rectifying channel, subfamily J, member 12 | NM_021012 |
| KCNJ13 | potassium inwardly-rectifying channel, subfamily J, member 13 | AJ007557 |
| KCNJ14 | potassium inwardly-rectifying channel, subfamily J, member 14 | NM_013348 |
| KCNJ15 | potassium inwardly-rectifying channel, subfamily J, member 15 | NM_002243 |

TABLE 2-continued

| Symbol | Name | Sequence ID |
|---|---|---|
| KCNJ16 | potassium inwardly-rectifying channel, subfamily J, member 16 | NM_018658 |
| KCNJ2 | potassium inwardly-rectifying channel, subfamily J, member 2 | NM_000891 |
| KCNJ3 | potassium inwardly-rectifying channel, subfamily J, member 3 | NM_002239 |
| KCNJ4 | potassium inwardly-rectifying channel, subfamily J, member 4 | NM_004981 |
| KCNJ5 | potassium inwardly-rectifying channel, subfamily J, member 5 | NM_000890 |
| KCNJ6 | potassium inwardly-rectifying channel, subfamily J, member 6 | NM_002240 |
| KCNJ8 | potassium inwardly-rectifying channel, subfamily J, member 8 | NM_004982 |
| KCNJ9 | potassium inwardly-rectifying channel, subfamily J, member 9 | NM_004983 |
| KCNJN1 | potassium inwardly-rectifying channel, subfamily J, inhibitor 1 | NM_002244 |
| KCNK1 | potassium channel, subfamily K, member 1 (TWIK-1) | NM_002245 |
| KCNK10 | potassium channel, subfamily K, member 10 | NM_021161 |
| KCNK12 | potassium channel, subfamily K, member 12 | NM_022055 |
| KCNK13 | potassium channel, subfamily K, member 13 | NM_022054 |
| KCNK2 | potassium channel, subfamily K, member 2 (TREK-1) | AF004711 |
| KCNK3 | potassium channel, subfamily K, member 3 (TASK-1) | NM_002246 |
| KCNK4 | potassium inwardly-rectifying channel, subfamily K, member 4 | NM_016611 |
| KCNK5 | potassium channel, subfamily K, member 5 (TASK-2) | NM_003740 |
| KCNK6 | potassium channel, subfamily K, member 6 (TWIK-2) | NM_004823 |
| KCNK7 | potassium channel, subfamily K, member 7 | NM_005714 |
| KCNK9 | potassium channel, subfamily K, member 9 (TASK-3) | NM_016601 |
| KCNMA1 | potassium large conductance calcium-activated channel, subfamily M, alpha member 1 | NM_002247 |
| KCNMB1 | potassium large conductance calcium-activated channel, subfamily M, beta member 1 | NM_004137 |
| KCNMB2 | potassium large conductance calcium-activated channel, subfamily M, beta member 2 | NM_005832 |
| KCNMB3 | potassium large conductance calcium-activated channel, subfamily M beta member 3 | NM_014407 |
| KCNMB3L | potassium large conductance calcium-activated channel, subfamily M, beta member 3-like | NM_014406 |
| KCNMB4 | potassium large conductance calcium-activated channel, subfamily M, beta member 4 | NM_014505 |
| KCNN1 | potassium intermediate/small conductance calcium-activated channel, subfamily N, member 1 | NM_002248 |
| KCNN2 | potassium intermediate/small conductance calcium-activated channel, subfamily N, member 2 | NM_021614 |
| KCNN3 | potassium intermediate/small conductance calcium-activated channel, subfamily N, member 3 | NM_002249 |
| KCNN4 | potassium intermediate/small conductance calcium-activated channel, subfamily N, member 4 | NM_002250 |
| KCNQ1 | potassium voltage-gated channel, KQT-like subfamily, member | NM_000218 |
| KCNQ2 | potassium voltage-gated channel, KQT-like subfamily, member | NM_004518 |
| KCNQ3 | potassium voltage-gated channel, KQT-like subfamily, member | NM_004519 |
| KCNQ4 | potassium voltage-gated channel, KQT-like subfamily, member | NM_004700 |
| KCNQ5 | potassium voltage-gated channel, KQT-like subfamily, member | NM_019842 |
| KCNS1 | potassium voltage-gated channel, delayed-rectifier, subfamily S, member 1 | NM_002251 |
| KCNS2 | potassium voltage-gated channel, delayed-rectifier, subfamily S, member 2 | AB032970 |
| KCNS3 | potassium voltage-gated channel, delayed-rectifier, subfamily S, member 3 | NM_002252 |

TABLE 2-continued

| Symbol | Name | Sequence ID |
|---|---|---|
| KIAA0439 | homolog of yeast ubiquitin-protein ligase Rsp5; potential epithelial sodium channel regulator | AB007899 |
| KIAA1169 | two-pore channel 1, homolog | NM_017901 |
| KV8.1 | neuronal potassium channel alpha subunit | NM_014379 |
| LOC64181 | two pore potassium channel KT3.3 | NM_022358 |
| OTRPC4 | vanilloid receptor-related osmotically activated channel; OTRPC4 protein | NM_021625 |
| P2RX1 | purinergic receptor P2X, ligand-gated ion channel, 1 | NM_002558 |
| P2RX2 | purinergic receptor P2X, ligand-gated ion channel, 2 | NM_012226<br>NM_016318 |
| P2RX3 | purinergic receptor P2X, ligand-gated ion channel, 3 | NM_002559 |
| P2RX4 | purinergic receptor P2X, ligand-gated ion channel, 4 | NM_002560 |
| P2RX5 | purinergic receptor P2X, ligand-gated ion channel, 5 | NM_002561 |
| P2RX7 | purinergic receptor P2X, ligand-gated ion channel, 7 | NM_002562 |
| SCN10A | sodium channel, voltage-gated, type X, alpha polypeptide | NM_006514 |
| SCN11A | sodium channel, voltage-gated, type XI, alpha polypeptide | AF188679 |
| SCN12A | sodium channel, voltage-gated, type XII, alpha polypeptide | NM_014139 |
| SCN1A | sodium channel, voltage-gated, type I, alpha polypeptide | AF225985 |
| SCN1B | sodium channel, voltage-gated, type I, beta polypeptide | NM_001037 |
| SCN2A2 | sodium channel, voltage-gated, type II, alpha 2 polypeptide | NM_021007 |
| SCN2B | sodium channel, voltage-gated, type II, beta polypeptide | NM_004588 |
| SCN3A | sodium channel, voltage-gated, type III, alpha polypeptide | AF225987 |
| SCN4A | sodium channel, voltage-gated, type IV, alpha polypeptide | NM_000334 |
| SCN5A | sodium channel, voltage-gated, type V, alpha polypeptide (long (electrocardiographic) QT syndrome 3) | NM_000335 |
| SCN6A | sodium channel, voltage-gated, type VI, alpha polypeptide | NM_002976 |
| SCN8A | sodium channel, voltage gated, type VIII, alpha polypeptide | NM_014191 |
| SCN9A | sodium channel, voltage-gated, type IX, alpha polypeptide | NM_002977 |
| SCNN1A | sodium channel, nonvoltage-gated 1 alpha | NM_001038 |
| SCNN1B | sodium channel, nonvoltage-gated 1, beta (Liddle syndrome) | NM_000336 |
| SCNN1D | sodium channel, nonvoltage-gated 1, delta | NM_002978 |
| SCNN1G | sodium channel, nonvoltage-gated 1, gamma | NM_001039 |
| TALK-1 | pancreatic 2P domain potassium channel TALK-1 | NM_032115 |
| TASK-4 | potassium channel TASK-4; potassium channel TALK-2 | NM_031460 |
| TRPC1 | transient receptor potential channel 1 | NM_003304 |
| TRPC2 | transient receptor potential channel 2 | X89067 |
| TRPC3 | transient receptor potential channel 3 | NM_003305 |
| TRPC4 | transient receptor potential channel 4 | NM_016179 |
| TRPC5 | transient receptor potential channel 5 | NM_012471 |
| TRPC6 | transient receptor potential channel 6 | NM_004621 |
| TRPC7 | transient receptor potential channel 7 | NM_003307 |
| VDAC1 | voltage-dependent anion channel 1 | NM_003374 |
| VDAC1P | voltage-dependent anion channel 1 pseudogene | AJ002428 |
| VDAC2 | voltage-dependent anion channel 2 | NM_003375 |
| VDAC3 | voltage-dependent anion channel 3 | NM_005662 |
| trp7 | putative capacitative calcium channel | NM_020389 |

BEST MODE FOR CARRYING OUT THE INVENTION

Figure 1:
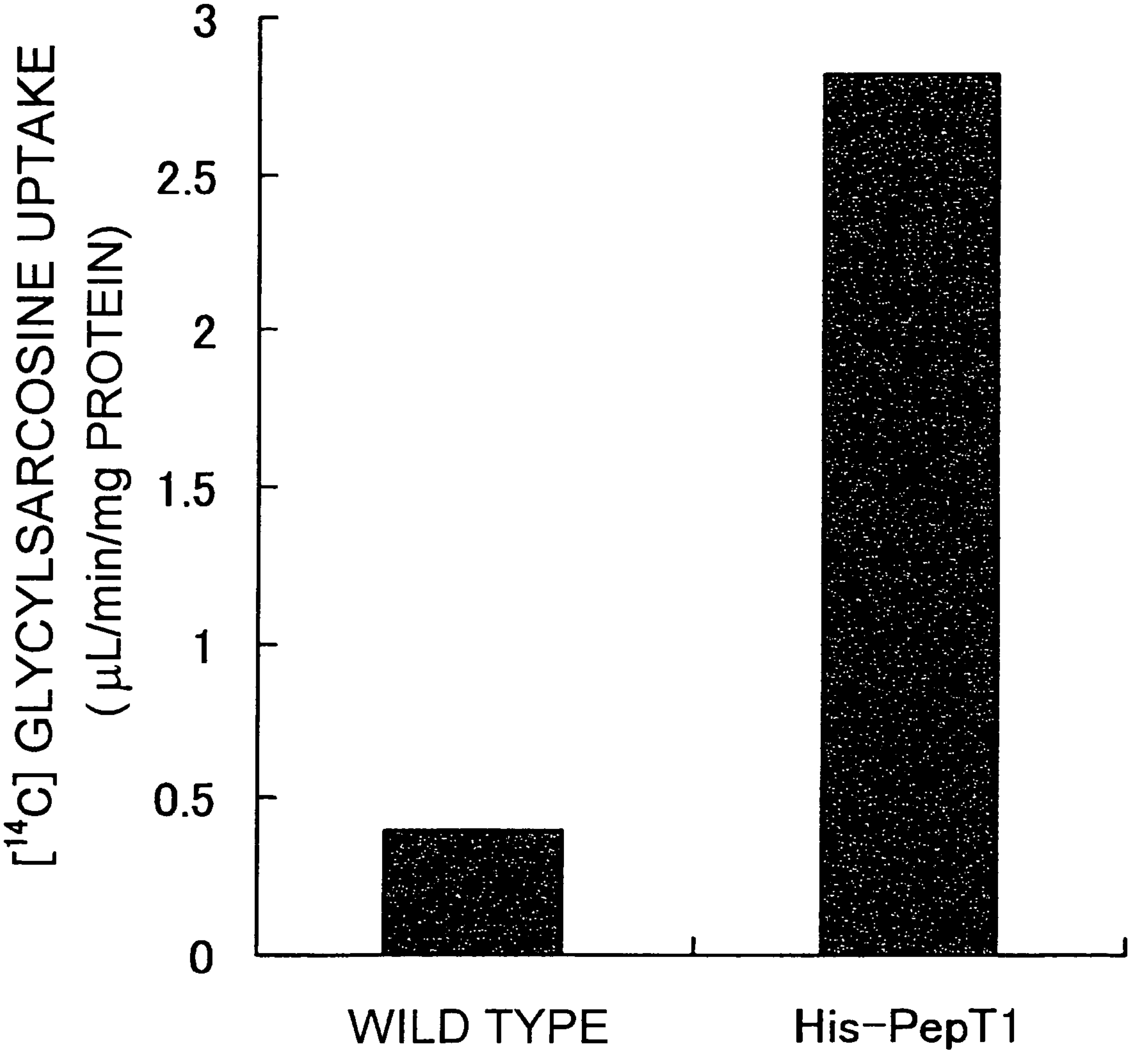
FIG. 1 is a graph showing PepT1 activity in PepT1-expressing viruses. The PepT1 activity on the viral envelope was measured as the amount of $^{14}$C glycylsarcosine uptake by the viruses. "Wild type" shows the amount taken up by the wild type virus. "His-PepT1" shows the amount taken up by a PepT1-expressing virus with a His-tag added to the N-terminal.

Herein below, the present invention will be specifically described using Examples, however, it is not to be construed as being limited to thereto.

EXAMPLE 1

1. Preparation of PepT1-expressing Budding Baculoviruses

A full-length PepT1 gene was isolated from a human kidney library using PCR. By inserting the full-length human PepT1 gene into pBlueBacHis2A (Invitrogen), the pBlueBacHis-PepT1 transfer vector was constructed. A Bac-N-Blue transfection kit (Invitrogen) was then used to introduce this transfer vector into Sf9 cells, along with Bac-N-Blue DNA. Thus, a recombinant virus for the expression of human PepT1 was constructed. Specifically, 4 μg of pBlueBacHis-PepT1 was added to Bac-N-Blue DNA, and then 1 mL of Grace's medium (GIBCO) and 20 μL of cell FECTIN reagent was added. This was mixed, incubated for 15 minutes at room temperature, and then added drop-by-drop to $2\times10^6$Sf9 cells washed once with the Grace's medium. After incubating for four hours at room temperature, 2 mL of complete medium (Grace's medium which comprises 10% fetal bovine serum (Sigma), 100 units/mL penicillin, and 100 μg/mL streptomycin (GIBCO-BRL)) was added and cultured at 27° C. Recombinant viruses for expressing human PepT1, which were constructed by homologous recombination, were cloned twice according to the instructions attached to the kit. A virus stock of the recombinant viruses was thus obtained.

Construction of budding-type viruses that express human PepT1 was carried out as follows. Specifically, 500 mL of Sf9 cells ($2\times10^6$/mL) were infected with the recombinant viruses prepared as above, so as to achieve MOI=5. After culturing at 27° C. for three days, the culture supernatant was centrifuged for 15 minutes at 800×g, and the cells and cell debris were removed. The supernatant recovered by centrifugation was centrifuged at 45,000×g for 30 minutes, and the precipitate was then suspended in PBS. The cellular components were removed by centrifuging for another 15 minutes at 800×g. The supernatant was again centrifuged at 45,000×g for 30 minutes, and the precipitate was again suspended in PBS. This suspension was the budding virus fraction. Expression of PepT1 in the virus and on the Sf-9 cell membrane was confirmed by Western analysis using anti-His antibodies. In addition, protein concentration was measured using Dc Protein Assay kit (Bio-Rad), with BSA as the standard.

2. PepT1 Functional Analysis $^{14}$C glycylsarcosine was diluted with HBSS (pH6.0) to a final concentration of 50 μM, and used as a substrate solution. 40 μL of viral solution (100 μg protein) was preincubated at 37° C. for 30 minutes. 160 μL of substrate solution that had been preheated to 37° C. was added, and the reaction was started. After one minute, 1 mL of ice-cold HBSS (pH 7.4) (hereinbelow also called "quenching solution") was added, and the reaction was stopped. The virus-comprising reaction solution was immediately vacuum filtered using a mixed cellulose membrane filter, and washed twice with 5 mL of the quenching solution. The membrane filter was transferred to a liquid scintillation vial, 5 mL of clear-zol I was added, and the filter was dissolved. After the dissolving, a liquid scintillation counter was used to measure radioactivity on the filter. Non-specific adsorption to the filter was measured in the same way for systems where the quenching solution was added before adding the substrate solution to the viral solution, and values thus obtained were subtracted from the counts for each experiment.

The PepT1 activity of the PepT1-expressing virus with a His-tag added at its N-terminal is shown in FIG. 1. A PepT1 activity ratio of about seven times that of the wild type virus not expressing PepT1 was detected.

EXAMPLE 2

1. Preparation of PepT2-expressing Budding Baculoviruses

The full-length PepT2 gene was isolated from a human kidney library. PCR was used to integrate the gene encoding the full-length human PepT2 into pBlueBacHis2A (Invitrogen), and a full-length PepT2 transfer vector (pBlueBac) was constructed. This vector was introduced into Sf-9 cells along with the viral DNA. After cloning the recombinant virus constructed by homologous recombination, a stock with a high recombinant virus activity was constructed. Sf-9 cells were infected with the stock virus, and after culturing for a certain period, PepT2 was expressed in the virus and on the membrane of Sf-P cells. PepT2 expression in the virus and on the membrane of the Sf-9 cells was confirmed by Western analysis using anti-His antibodies. More specifically, except for using the PepT2 gene, operations were carried out according to the methods described in Example 1.

2. PepT2 Functional Analysis $^{3}$H glycylsarcosine was diluted with HBSS (pH6.0) to a final concentration of 0.8 μM, and used as a substrate solution. 40 μL of viral solution (100 μg protein) was preincubated at 37° C. for 30 minutes. 160 μL of the substrate solution preheated to 37° C. was added to commence the reaction. After one minute, 1 mL of the quenching solution was added, and the reaction was stopped. The virus-comprising reaction solution was immediately vacuum filtered using a mixed cellulose membrane filter, and washed twice with 5 mL of the quenching solution. The membrane filter was transferred to a liquid scintillation vial, 5 mL of clear-sol I was added, and the filter was dissolved. After the dissolving, a liquid scintillation counter was used to measure radioactivity on the filter. The quenching solution was added before adding the substrate solution to the viral solution, and similar manipulations were performed. Non-specific adsorption to the filter was measured and the obtained value was subtracted from the counts for each experiment.

Figure 2:
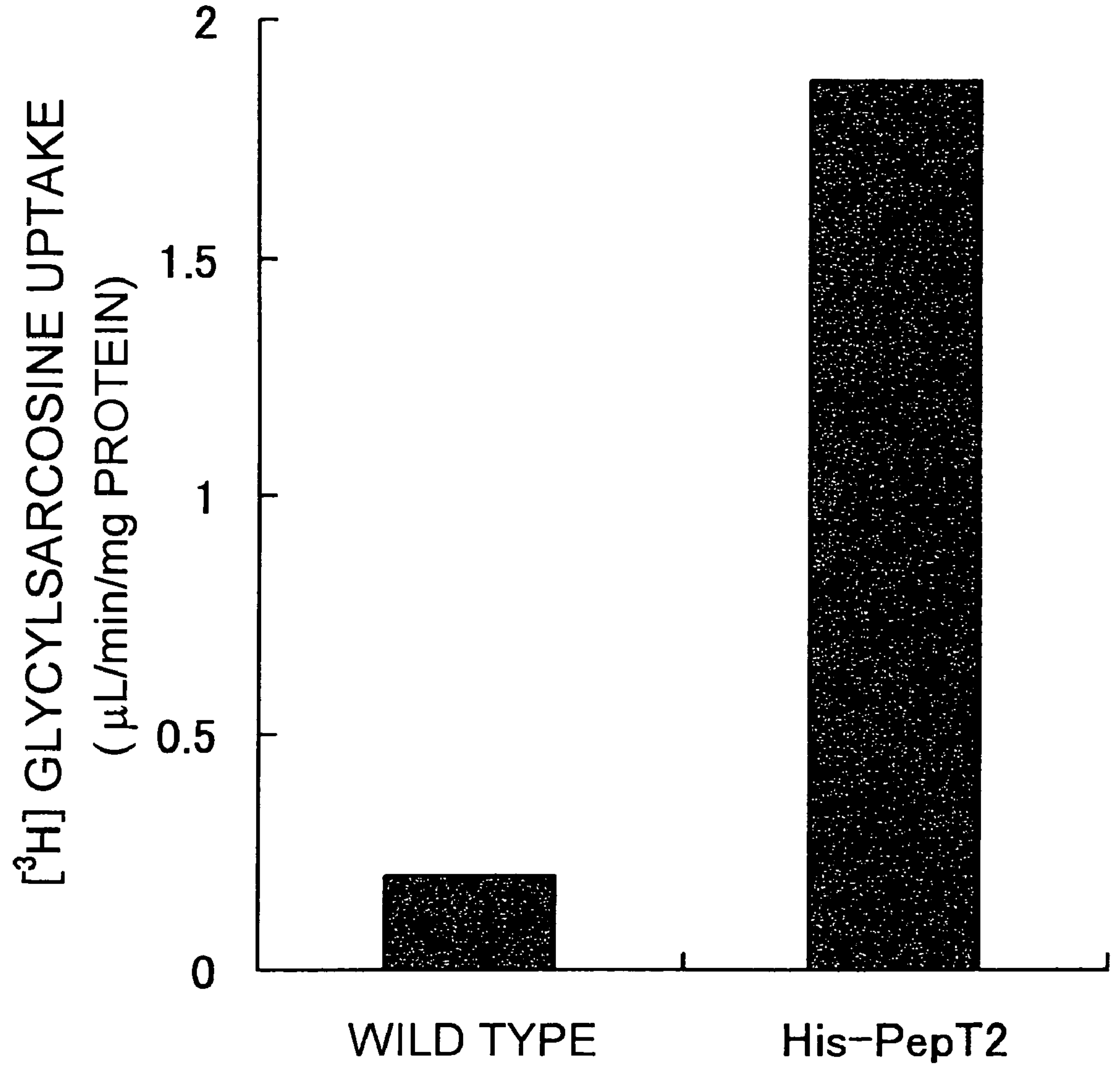
FIG. 2 is a graph showing PepT2 activity in PepT2-expressing viruses. The PepT2 activity on the viral envelope was measured as the amount of $^{3}$H glycylsarcosine uptake by viruses. "Wild type" shows the amount taken up by the wild type virus. "His-PepT2" shows the amount taken up by a PepT2-expressing virus with a His-tag added to the N-terminal.

The PepT2 activity of the PepT2-expressing virus with a His-tag added to its N-terminal is shown in FIG. 2. A PepT2 activity ratio of about nine times that of the wild type virus not expressing PepT2 was detected.

EXAMPLE 3

1. Preparation of OATP-C Expressing Baculoviruses cDNA encoding wild type human OATP-C (OATP-C WT) was cloned as follows. Specifically, adult human liver-derived cDNA was used as a template, and the OATP-C WT cDNA was divided into two fragments and amplified using PCR with the following primer combinations:

```
5' side
OAHC17 primer. 5' gat ggt acc aaa    (SEQ ID NO: 1)
               ctg agc atc aac aac
               aaa aac 3'
OAHC18 primer: 5' gat ggt acc cat    (SEQ ID NO: 2)
               cga gaa tca gta gga
               gtt atc 3'

3' side
OAHC21 primer: 5' gat ggt acc tac    (SEQ ID NO: 3)
               cct ggg atc tct gtt
               ttc taa 3'
OAHC22 primer: 5' gat ggt acc gtt    (SEQ ID NO: 4)
               tgg aaa cac aga agc
               aga agt 3'
```

Each of these fragments were subcloned to pT7Blue-T vector (Novagen), and clones without PCR errors were selected. Both were linked at the BglII site which exists in an overlapping region, and then cleaved at the KpnI site that exists on both ends. After incorporation at the KpnI site of pcDNA3 vector (Invitrogen), pcDNA3/OATP-C WT was obtained.

Next, with pcDNA3/OATP-C WT as a template, in vitro mutageneis using GeneEditor™ (Promega) was used to prepare cDNAs coding for OATP-C N130D in which the 130$^{th}$ asparagine was mutated to aspartic acid, and OATP-C V174A in which the 174$^{th}$ valine was mutated to alanine. The primers used for mutagenesis were as follows:

```
Primer for OATP-C N130D:
5' gaa act aat atc gat tca tca gaa   (SEQ ID NO: 5)
aat 3'

Primer for OATP-C V174A:
5' atg tgg ata tat gcg ttc atg ggt   (SEQ ID NO: 6)
aat 3'
```

The primers for use in mutagenesis and the selection primers included in kits (for bottom strand use) were both annealed to the template plasmid DNA, which had been made into a single strand. Thus, a new DNA strand was constructed. This was introduced into *E. coli*, and GeneEditor™ antibiotic-resistant clones were obtained. These clones were sequenced and clones containing mutations were thus selected (pcDNA3/OATP-C N130D and pcDNA3/OATP-C V174A).

Next, using pcDNA3/OATP-C WT, pcDNA3/OATP-C N130D and pcDNA3/OATP-CV174A as respective templates, PCR was carried out using the primers below, thus amplifying the respective cDNAs with SalI sites on each end.

```
C45 primer: 5' gat gtc gac tta aca   (SEQ ID NO 7)
            atg tgt ttc act 3'

C58 primer: 5' gat gtc gac tat gga   (SEQ ID NO: 8)
            cca aaa tca aca t 3'
```

These were digested with SalI, and then inserted into the SalI site of the pBlueBac His2A vector (Invitrogen). Thus transfer vectors encoding each OATP-C protein with a His-tag attached at the N-terminal were constructed (pBlueBac His2A/OATP-C WT, pBlueBac His2A/OATP-C N130D, pBlueBac His2A/OATP-C V174A).

Using Bac-N-Blue transfection kit (Invitrogen), these vectors were introduced into Sf-9 cells along with viral DNA. After five to eight days, plaque assays were used to clone the recombinant viruses in the culture supernatant. The viruses were then amplified, and a stock of highly active recombinant viruses was prepared. Sf-9 cells were infected with the stock viruses at MOI=1. After four days, recombinant viruses were recovered from the culture supernatant. OATP-C expression on the viral envelope was confirmed by Western analysis using anti-His antibodies.

2. OATP-C Functional Analysis.

$^{3}$H estrone sulphate conjugate was diluted with HBSS (pH7.4) to a final concentration of 10 nM, and used as a substrate solution. 20 μL of viral solution (50 μg protein) was preincubated at 37° C. for 30 minutes. 180 μL of the substrate solution preheated to 37° C. was added, and the reaction was started. After one minute, 1 mL of ice-cold HBSS (pH7.4) (hereinafter referred to as "quenching solution") was added, and the reaction was stopped. The virus-comprising reaction solution was immediately vacuum filtered using a mixed cellulose membrane filter, and washed twice with 5 mL of the quenching solution. The membrane filter was transferred to a liquid scintillation vial, 5 mL of clear-sol I was added, and the filter was dissolved. After the dissolving, a liquid scintillation counter was used to measure radioactivity on the filter. To measure non-specific adsorption to the filter, the reaction quenching solution was added before adding the substrate solution and similar manipulations were performed. The obtained value was subtracted from the counts for each experiment.

Figure 3:
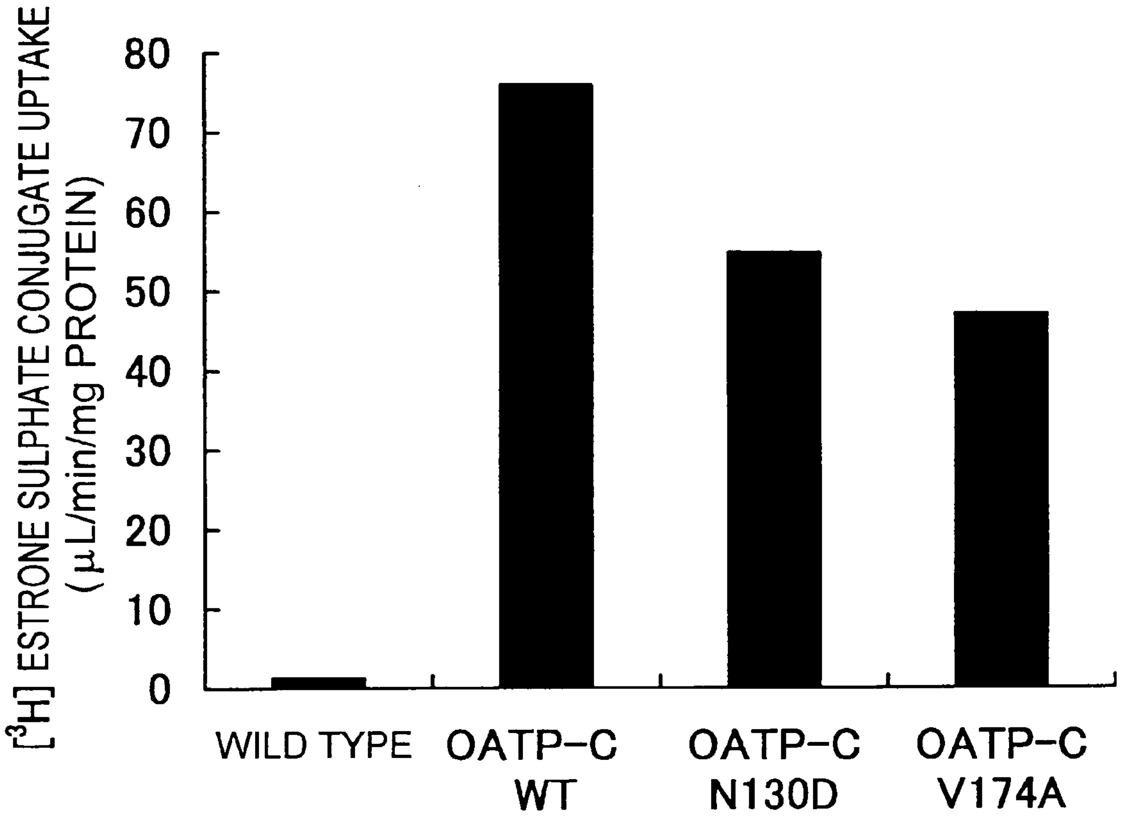
FIG. 3 is a graph showing OATP-C activity in OATP-C-expressing viruses. The OATP-C activity on the viral envelope was measured as the amount of $^{3}$H estrone sulphate conjugate taken up by viruses. "Wild type" shows the amount taken up by the wild type virus. "OATP-C WT" shows the amount taken up by a wild-type OATP-C-expressing virus. "OATP-C N130D" shows the amount taken up by a N130D mutant OATP-C-expressing virus. "OATP-C V147A" shows the amount taken up by a V147A mutant OATP-C-expressing virus. Each of these OATP-Cs comprises a His-tag added to the N-terminal.

The activity of $^{3}$H estrone sulphate conjugate uptake is shown in FIG. 3 for three types of OATP-C-expressing viruses with His-tags added to their N-terminals. The detected $^{3}$H estrone sulphate conjugate uptake activity ratios for wild type OATP-C, N130D, and V174A were respectively 57, 41, and 36 times that of a wild type virus not expressing OATP-C. In addition, virus-derived endogenous OATP-C activity was hardly detected in experiments on the uptake in wild type viruses. Thus, it was revealed that budding baculovirus expression systems are systems with extremely low background levels. Furthermore, since OATP-C mutants (N130D, V174A) can be functionally expressed on viral envelopes, changes in substrate specificity due to SNPs can also be determined, making also applications to tailor-made therapy possible.

EXAMPLE 4

Search for PepT1 Function Inhibiting Antibodies $^{14}C$ glycylsarcosine was diluted with HBSS (pH 6.0) to a final concentration of 50 μM, and used as a substrate solution. In addition, a mouse monoclonal antibody recognising the extracellular region of human PepT1 was diluted with PBS to a final concentration of 200 μg/mL, and used as an antibody solution. 20 μL (50 μg protein) of solution of budding baculoviruses expressing PepT1 with a His-tag added at the N-terminal was mixed with 20 μL of the antibody solution and incubated for one hour at 37° C. 160 μL of substrate solution preheated to 37° C. was added, and the reaction was started. After one minute, 1 mL of ice-cold HBSS (pH 7.4) (below also called "quenching solution") was added, and the reaction was stopped. The virus-comprising reaction solution was immediately vacuum filtered using a mixed cellulose membrane filter, and washed twice with 5 mL of the quenching solution. The membrane filter was transferred to a liquid scintillation vial, 5 mL of clear-sol I was added, and the filter was dissolved. After the dissolving, a liquid scintillation counter was used to measure radioactivity on the filter. Non-specific adsorption to the filter was measured by adding the reaction quenching solution before adding the substrate solution to the viral solution, and performing similar manipulations. The obtained value was subtracted from the counts for each experiment.

Figure 4:
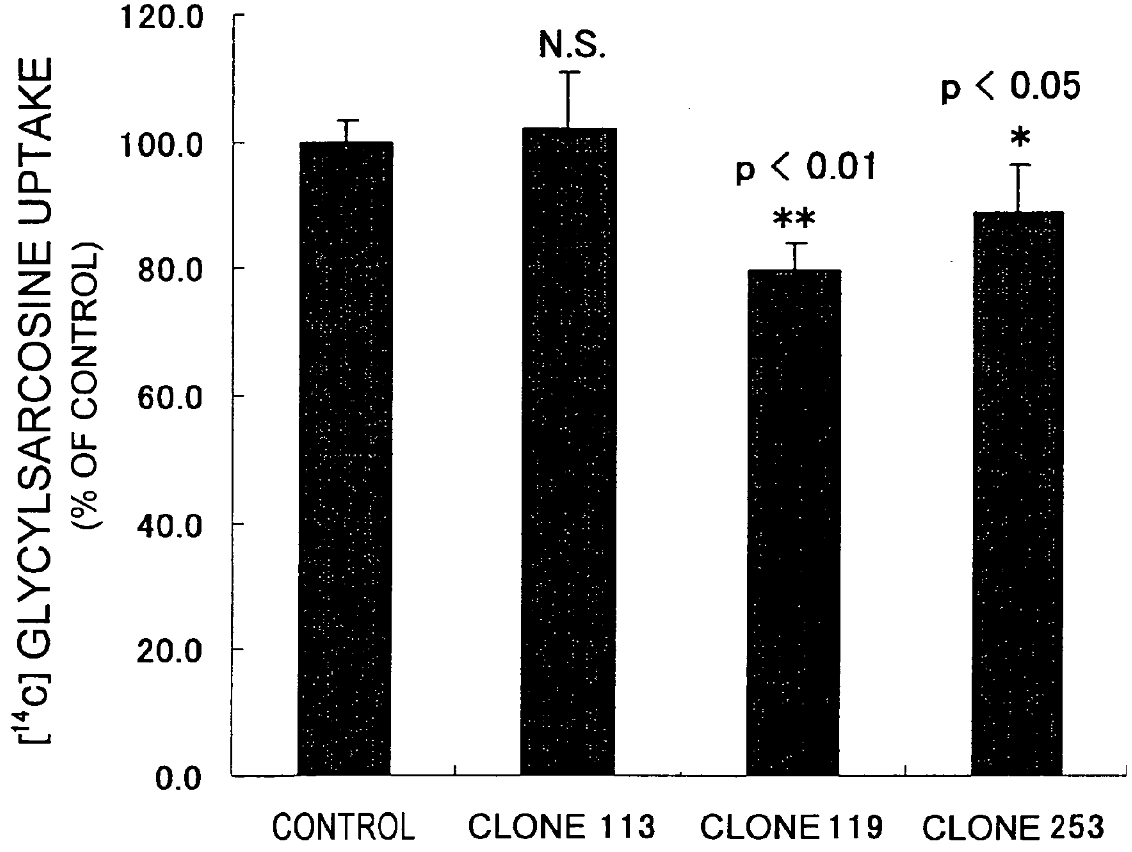
FIG. 4 is a graph showing the results of detecting inhibition of the PepT1 activity in PepT1-expressing viruses by an anti-human PepT1 monoclonal antibody. The PepT1 activity on the viral envelope was measured as the amount of $^{14}$C glycylsarcosine taken up by the viruses. Data is shown as the mean+/−SD (n=3-4).

The PepT1 activity inhibition by the anti-human PepT1 monoclonal antibodies is shown in FIG. 4. PepT1 activity in the absence of the antibodies was taken as the control and expressed as 100. Of the three types of anti-human PepT1 monoclonal antibodies, clone 119 inhibited PepT1 activity by about 20%, and clone 253 by about 10%, compared to the control. This PepT1 activity inhibition was statistically significant (Student t-test). Thus, budding baculovirus expression systems will be useful in the search for substrates that inhibit or promote transporter activity.

INDUSTRIAL APPLICABILITY

The present invention provides viruses that express transporters having transporter activity, and by using these viruses, transporter activity can be measured with a high sensitivity and less background level than in the past. Thus, it is expected that by employing the methods of the present invention, identification of transport substrates and driving force of transporters, and functional analysis such as kinetic analysis can be carried out more easily and accurately than before. In addition, by using such viruses, substances that inhibit or promote the transport activities of transporters expressed on the viral envelopes can be screened. Since transporters have also been reported to be involved in the transport of drugs into cells, substances that inhibit or promote the activities of transporters associated with diseases can become candidates for new pharmaceutical agents. Furthermore, by using the methods of the present invention for analysis of SNPs in transporter-encoding genes, functional changes due to transporter SNPs can be measured over a more extensive range of substrates. Application to tailor-made therapies is also possible since response to a drug can be analyzed for each individual.

The invention claimed is:

1. A method for preparing a budding virus expressing a mammalian transporter having transporter activity, the method comprising (a) culturing a host cell that (i) is infected with a budding virus that comprises a gene encoding the transporter and (ii) is recombinantly expressing the transporter;

(b) expressing the transporter on the envelope of a budding virus released from the host cell; and (c) harvesting the released virus, wherein the transporter on the envelope of the released virus has transporter activity.

2. The method of claim 1, wherein the virus is a baculovirus.

3. The method of claim 1, wherein the transporter is a peptide transporter or an organic anion transporter.

4. The method of claim 1, wherein the transporter is H+/di-tripeptide transporter 1 (PepT1), H+/di-tripeptide transporter 2 (PepT2), or organic anion-transporting polypeptide-C (OATP-C).

5. The method of claim 1, wherein the host cell is an insect cell.

6. The method of claim 5, wherein the insect cell is an Sf9 cell.

7. The method of claim 1, further comprising assaying the harvested virus for activity of the transporter.

8. The method of claim 1, further comprising confirming that the transporter on the envelope of the harvested virus possesses transport activity.

9. The method of claim 1, further comprising using the harvested virus in an assay for detecting whether a test compound is transported by the transporter.

10. The method of claim 1, wherein the budding virus of (a) is a recombinant budding virus comprising a gene encoding the transporter.

11. A purified baculovirus, the envelope of which comprises a mammalian transporter having transporter activity.

12. The baculovirus of claim 11, wherein the transporter is a peptide transporter or an organic anion transporter.

13. The baculovirus of claim 12, wherein the transporter is PepT1, PepT2, or OATP-C.

14. A method for measuring the activity of a mammalian transporter, the method comprising (a) providing a budding baculovirus the envelope of which comprises a mammalian transporter having transporter activity; and (b) measuring the activity of the mammalian transporter.

15. The method of claim 14, wherein the transporter is a peptide transporter or an organic anion transporter.

16. The method of claim 15, wherein the transporter is PepT1, PepT2, or OATP-C.

17. A method of screening for a substance that inhibits or promotes transport activity of a mammalian transporter, the method comprising (a) providing a budding baculovirus the envelope of which comprises a mammalian transporter having transporter activity;

(b) contacting the transporter with a test substance, and (c) selecting a substance that inhibits or promotes the transport activity.

18. The method of claim 17, wherein the transporter is a peptide transporter or an organic anion transporter.

19. The method of claim 18, wherein the transporter is PepT1, PepT2, or OATP-C.

20. The method of claim 17, which comprises immobilizing the virus on a support.

21. The method of claim 20, wherein the virus is immobilized on the support through an antibody against an envelope protein expressed on the viral envelope.

22. The method of claim 20, wherein the virus is immobilized on the support through a biotin-streptavidin reaction by biotinylating a protein expressed on the viral envelope.

* * * * *

UNITED STATES PATENT AND TRADEMARK OFFICE

CERTIFICATE OF CORRECTION

PATENT NO. : 7,666,610 B2
APPLICATION NO. : 10/509343
DATED : February 23, 2010
INVENTOR(S) : Saitoh et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 227 days.

Signed and Sealed this

Seventh Day of December, 2010

David J. Kappos
*Director of the United States Patent and Trademark Office*

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 1

gatggtacca aactgagcat caacaacaaa aac                              33


<210> SEQ ID NO 2
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 2

gatggtaccc atcgagaatc agtaggagtt atc                              33


<210> SEQ ID NO 3
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 3

gatggtacct accctgggat ctctgttttc taa                              33
```

-continued

```
<210> SEQ ID NO 4
<211> LENGTH: 33
<212> TYPE: DNA
<213> ORGANISM: Artificial
<220> FEATURE:
<223> OTHER INFORMATION: an artificially synthesized primer sequence

<400> SEQUENCE: 4

gatggtaccg tttggaaaca cagaagcaga agt                                33


<210> SEQ ID NO 5
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 5

gaaactaata tcgattcatc agaaaat                                       27


<210> SEQ ID NO 6
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 6

atgtggatat atgcgttcat gggtaat                                       27


<210> SEQ ID NO 7
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 7

gatgtcgact taacaatgtg tttcact                                       27


<210> SEQ ID NO 8
<211> LENGTH: 28
<212> TYPE: DNA
<213> ORGANISM: Artificial
<220> FEATURE:
<223> OTHER INFORMATION: an artificially synthesized primer sequence

<400> SEQUENCE: 8

gatgtcgact atggaccaaa atcaacat                                      28
```